US011773401B2

(12) United States Patent
Yuan et al.

(10) Patent No.: US 11,773,401 B2
(45) Date of Patent: Oct. 3, 2023

(54) BZIP TRANSCRIPTION FACTORS REGULATE CONVERSION OF NICOTINE TO NORNICOTINE

(71) Applicants: University of Kentucky Research Foundation, Lexington, KY (US); R.J. REYNOLDS TOBACCO COMPANY, Winston-Salem, NC (US)

(72) Inventors: Ling Yuan, Lexington, KY (US); Sanjay K. Singh, Lexington, KY (US); Sitakanta Pattanaik, Lexington, KY (US); Darlene Madeline Lawson, Kernersville, NC (US)

(73) Assignees: University of Kentucky Research Foundation, Lexington, KY (US); R.J. Reynolds Tobacco Company, Winston-Salem, NC (US)

( * ) Notice: Subject to any disclaimer, the term of this patent is extended or adjusted under 35 U.S.C. 154(b) by 456 days.

(21) Appl. No.: 16/770,906

(22) PCT Filed: Dec. 6, 2018

(86) PCT No.: PCT/US2018/064317
§ 371 (c)(1),
(2) Date: Jun. 8, 2020

(87) PCT Pub. No.: WO2019/113360
PCT Pub. Date: Jun. 13, 2019

(65) Prior Publication Data
US 2021/0171967 A1 Jun. 10, 2021

Related U.S. Application Data

(60) Provisional application No. 62/595,983, filed on Dec. 7, 2017.

(51) Int. Cl.
*C12N 15/82* (2006.01)
*C12N 15/113* (2010.01)
*A01H 5/12* (2018.01)

(52) U.S. Cl.
CPC .......... *C12N 15/8218* (2013.01); *A01H 5/12* (2013.01); *C12N 15/113* (2013.01); *C12N 2310/11* (2013.01); *C12N 2310/141* (2013.01); *C12N 2310/3231* (2013.01)

(58) Field of Classification Search
None
See application file for complete search history.

(56) References Cited

U.S. PATENT DOCUMENTS

| | | | |
|---|---|---|---|
| 7,795,503 B2 * | 9/2010 | Apuya | C12N 15/8243 800/312 |
| 2006/0195934 A1 | 8/2006 | Apuya et al. | |
| 2007/0006335 A1 | 1/2007 | Cook et al. | |
| 2009/0070899 A1 * | 3/2009 | Apuya | C12N 15/8216 800/278 |
| 2016/0057967 A1 | 3/2016 | Dewey et al. | |

FOREIGN PATENT DOCUMENTS

| | | |
|---|---|---|
| CN | 105602961 A1 | 5/2016 |
| WO | WO 2008/118394 A1 | 10/2008 |
| WO | WO 2011/088180 A1 | 7/2011 |
| WO | WO 2015/169927 A1 | 11/2015 |

OTHER PUBLICATIONS

Li et al, 2021, Agronomy, 11:1-17.*
Lewis et al, 2008, Plant Biotechnology, 6:346-354.*
Lewis et al, 2010, Phytochemistry, 71:1988-1998.*
Siminszky, et al., Conversion of nicotine to nornicotine in Nicotiana tabacum is mediated by CYP82E4, a cytochrome P450 monooxygenase, PNAS, Oct. 11, 2005, vol. 102, No. 41, pp. 14919-14924.
Lewis et al. "RNA interference (RNAi)-Induced Suppression of Nicotine Demethylase Activity Reduces Levels of a Key Carcinogen in Cured Tobacco Leaves," Plant Biotechnology Journal, Feb. 14, 2008 (Feb. 14, 2008), vol. 6, No. 4, pp. 346-354.
Pakdeechanuan et al. "Non-Functionalization of Two CYP82E Nicotine N-Demethylase Genes Abolishes Nornicotine Formation in Nicotiana langsdorffii," Plant and Cell Physiology, Oct. 3, 2012 (Oct. 3, 2012), vol. 53, No. 12, pp. 2038-2046.
Chakrabarti et al. "CYP82E4-Mediated Nicotine to Nornicotine Conversion in Tobacco is Regulated by a Senescence-Specific Signaling Pathway," Plant Mol Biol, Jan. 15, 2008 (Jan. 15, 2008), vol. 66, pp. 415-427.
Schindler et al. "TGA1 and G-Box Binding Factors: Two Distinct Classes of Arabidopsis Leucine Zipper Proteins Compete for the G-Box-Like Element TGACGTGG," The Plant Cell, Oct. 1, 1992 (Oct. 1, 1992), vol. 4, No. 10, pp. 1309-1319.
Li et al. "Development of CAPS and dCAPS Markers for CYP82E4, CYP82E5v2 and CYP82E10 Gene mutants Reducing Nicotine to Nornicotine Conversion in Tobacco," Molecular Breeding, Apr. 11, 2011 (Apr. 11, 2011), vol. 29, No. 3, pp. 589-599.
Xu et al. "Wild tobacco genomes reveal the evolution of nicotine biosynthesis," Proc. Natl. Acad. Sci. U.S.A. May 23, 2017 (May 23, 2017), vol. 114, No. 23, pp. 6133-6138.

(Continued)

*Primary Examiner* — Jason Deveau Rosen
(74) *Attorney, Agent, or Firm* — Stites & Harbison PLLC; Mandy Wilson Decker

(57) ABSTRACT

A method of decreasing conversion of nicotine to nornicotine is provided herein. The methods includes administering at least one basic region/leucine zipper (bZIP) type transcription factor inhibitor to an organism in need thereof. Also provided herein is a method of decreasing conversion of nicotine to nornicotine including mutating a bZIP type transcription factor binding site on a promoter of a nicotine N-demethylase (NND). Further provided herein is a method of decreasing conversion of nicotine to nornicotine including mutating a plant genome to knockout at least one bZIP type transcription factor.

8 Claims, 16 Drawing Sheets
Specification includes a Sequence Listing.

(56) References Cited

OTHER PUBLICATIONS

Lewis RS et al: 11 Three nicotine demethylase genes mediate nornicotine biosynthesis in *Nicotiana tabacum* L.: Functional characterization of the CYP82E10 gene, Phytochemistry, Elsevier, Amsterdam, NL, vol. 71, No. 17-18, Dec. 1, 2010 (Dec. 1, 2010), pp. 1988-1998.

Liedschulte Verena et al: 11 Identification of CYP82E21 as a functional nicotineN-demethylase in tobacco flowers, Phytochemistry, Elsevier, Amsterdam, NL, vol. 131, Sep. 3, 2016 (Sep. 3, 2016), pp. 9-16.

\* cited by examiner

FIG. 6

SD-Leu-Trp    SD-Leu-Trp-His-Ade

1. AD-NtbZIP1a$^{aa\,1-144}$ + BD-NtbZIP2a$^{aa\,1-1455}$
2. AD-NtbZIP1b$^{aa\,1-144}$ + BD-NtbZIP2a$^{aa\,1-1455}$
3. AD-NtbZIP2a$^{aa\,1-455}$ + BD-NtbZIP2a$^{aa\,1-1455}$
4. AD (empty vector) + BD-BD-NtbZIP2a$^{aa\,1-1455}$ NtbZIP1 (amino acid 1-144)

NtbZIP2 (amino acid 1-455)

SEQUENCE LISTING

<160> NUMBER OF SEQ ID NOS: 6

<210> SEQ ID NO 1
<211> LENGTH: 435
<212> TYPE: DNA
<213> ORGANISM: Nicotiana tabacum

<400> SEQUENCE: 1

```
atggctttga cacagcaacc ggctagttca ggttctgatg gccaacgtta tgccacaaat      60
gacgatagaa aacgaaagag aatggagtcc aaccgtgaat ctgcaaggcg gtcacggatg     120
agaaagcagc agcatttgga ggagttgatg agccaaatga cacagctaca gaatcagaac     180
gttctgtggc gcgagaagat tgatgctgtg ggaagaaact acctcaccct cgatgcggag     240
aacaatgtct tgagggctca aatggcagaa ctgactgaac gcttggattc tctcaattcg     300
ctcactcgtt tctgggctga tgctaatgga ctagctgtgg atatccctga aattcctgac     360
actttgcttg agccctggca gcttccttgc ccaattcaac ccatcactgc ttctgctgat     420
atgtttcagt tttga                                                     435
```

<210> SEQ ID NO 2
<211> LENGTH: 144
<212> TYPE: PRT
<213> ORGANISM: Nicotiana tabacum

<400> SEQUENCE: 2

```
Asn Ala Leu Thr Gln Gln Pro Ala Ser Ser Gly Ser Asp Gly Gln Arg
1               5                   10                  15

Tyr Ala Thr Asn Asp Asp Arg Lys Arg Lys Arg Met Glu Ser Asn Arg
                20                  25                  30

Glu Ser Ala Arg Arg Ser Arg Met Arg Lys Gln Gln His Leu Glu Glu
            35                  40                  45

Leu Met Ser Gln Met Thr Gln Leu Gln Asn Gln Asn Val Leu Trp Arg
        50                  55                  60

Glu Lys Ile Asp Ala Val Gly Arg Asn Tyr Leu Thr Leu Asp Ala Glu
65                  70                  75                  80

Asn Asn Val Leu Arg Ala Gln Met Ala Glu Leu Thr Glu Arg Leu Asp
                85                  90                  95

Ser Leu Asn Ser Leu Thr Arg Phe Trp Ala Asp Ala Asn Gly Leu Ala
            100                 105                 110

Val Asp Ile Pro Glu Ile Pro Asp Thr Leu Leu Glu Pro Trp Gln Leu
        115                 120                 125

Pro Cys Pro Ile Gln Pro Ile Thr Ala Ser Ala Asp Met Phe Gln Phe
    130                 135                 140
```

<210> SEQ ID NO 3
<211> LENGTH: 435
<212> TYPE: DNA
<213> ORGANISM: Nicotiana tabacum

<400> SEQUENCE: 3

```
atggcttcga tacagcaacc agctagttca ggttctgatg gccaacgata tgctatgaac      60
gacgatagaa aacgaaagag aatggagtcc aaccgtgaat ctgcaaggcg gtcacggatg     120
aggaagcagc agcatttgga agagttgatg agccaaatga cacagctaca gaatcagaac     180
gttctgtggc gtgagaagat tgatgctgtg ggaagaaact acctgaccct tgatgcggag     240
aacaatgtcc tgagggctca aatggcagaa ctgactgaac gcttggattc gctcaattcg     300
```

-continued

```
ctcgctcgtt tctgggctga tgctaatgga ctagctgtgg atatccctga aattccagac    360
actttgcttg agccgtggca gcttccttgc ccaattcaac ccatcactgc ttctgctaat    420
atgtttcagt tttga                                                     435
```

<210> SEQ ID NO 4
<211> LENGTH: 144
<212> TYPE: PRT
<213> ORGANISM: Nicotiana tabacum

<400> SEQUENCE: 4

Asn Ala Ser Ile Gln Gln Pro Ala Ser Gly Ser Asp Gly Gln Arg
1               5                   10                  15

Tyr Ala Met Asn Asp Asp Arg Lys Arg Lys Arg Met Glu Ser Asn Arg
            20                  25                  30

Glu Ser Ala Arg Arg Ser Arg Met Arg Lys Gln Gln His Leu Glu Glu
        35                  40                  45

Leu Met Ser Gln Met Thr Gln Leu Gln Asn Gln Asn Val Leu Trp Arg
    50                  55                  60

Glu Lys Ile Asp Ala Val Gly Arg Asn Tyr Leu Thr Leu Asp Ala Glu
65              70                  75                  80

Asn Asn Val Leu Arg Ala Gln Met Ala Glu Leu Thr Glu Arg Leu Asp
            85                  90                  95

Ser Leu Asn Ser Leu Ala Arg Phe Trp Ala Asp Ala Asn Gly Leu Ala
        100                 105                 110

Val Asp Ile Pro Glu Ile Pro Asp Thr Leu Leu Glu Pro Trp Gln Leu
    115                 120                 125

Pro Cys Pro Ile Gln Pro Ile Thr Ala Ser Ala Asn Met Phe Gln Phe
130                 135                 140

<210> SEQ ID NO 5
<211> LENGTH: 455
<212> TYPE: PRT
<213> ORGANISM: Nicotiana tabacum

<400> SEQUENCE: 5

Met Asp Arg Val Phe Ser Val Asp Asp Ile Gly Asp His Phe Trp
1               5                   10                  15

Ser Thr Pro Pro Thr Ala Asp Leu Gly Val Asp Ser Pro Thr Ala Ala
            20                  25                  30

Ala Val Ser Tyr Ser Lys Met Met Asn Arg Ser Ser Ser Glu Trp
        35                  40                  45

Ala Phe Gln Arg Phe Leu Gln Glu Ala Thr Ala Ala Gly Thr Ser Thr
    50                  55                  60

Ser Ser Pro Pro Gln Pro Pro Thr Met Thr Ala Ser Ser Ser Ser
65              70                  75                  80

Ser His Gln Asn Asp Val Val Glu Ile Lys Asp Glu Asn Leu Ser Ile
            85                  90                  95

Pro Asn Leu Asn Pro Ser Thr Ala Leu Asn Ser Lys Pro Ala Ser Ser
        100                 105                 110

Phe Gly Leu Ala Pro Pro Asn Ile Ala Val Asp Ser Glu Glu Tyr
    115                 120                 125

Gln Ala Phe Leu Lys Ser Gln Leu His Leu Ala Cys Ala Ala Val Ala
130                 135                 140

Leu Thr Arg Gly Lys Ser Leu Asn Pro Gln Asp Ser Gly Ser Thr Ala
145                 150                 155                 160

-continued

His Asp Lys Gly Ser Glu Thr Ala Ser Ala Gln Ser Gly Ser His
             165                 170                 175

Val Ser Thr Leu Gly Lys Cys Tyr Leu Arg Ser Gly Gln Glu Val Ala
         180                 185                 190

Lys Ile Gln Asp Lys Asp Ala Gly Gly Pro Val Gly Ile Pro Ser Leu
             195                 200                 205

Pro Pro Val Gln Lys Lys Pro Val Gln Val Arg Ser Thr Thr Ser
210                 215                 220

Gly Ser Ser Arg Glu Gln Ser Asp Asp Glu Ala Glu Gly Glu Ala
225                 230                 235                 240

Glu Thr Thr Gln Gly Met Asp Pro Ala Asp Ala Lys Arg Val Arg Arg
                 245                 250                 255

Met Leu Ser Asn Arg Glu Ser Ala Arg Arg Ser Arg Arg Arg Lys Gln
             260                 265                 270

Ala His Leu Thr Glu Leu Glu Thr Gln Val Ser Gln Leu Arg Val Glu
         275                 280                 285

Asn Ser Ser Leu Leu Lys Arg Leu Thr Asp Ile Ser Gln Lys Tyr Asn
             290                 295                 300

Glu Ala Ala Val Asp Asn Arg Val Leu Lys Ala Asp Val Glu Thr Leu
305                 310                 315                 320

Arg Ala Lys Val Lys Met Ala Glu Thr Val Lys Arg Val Thr Gly
                 325                 330                 335

Leu Asn Pro Leu Phe Gln Ala Met Ser Glu Ile Ser Ser Met Val Met
             340                 345                 350

Pro Ser Tyr Ser Gly Ser Pro Ser Asp Thr Ser Ala Asp Ala Ala Val
         355                 360                 365

Pro Val Gln Asp Asp Pro Lys His His Tyr Tyr Gln Gln Pro Pro Asn
370                 375                 380

Asn Leu Met Pro Thr His Asp Pro Arg Ile Gln Asn Gly Met Val Asp
385                 390                 395                 400

Val Pro Pro Ile Glu Asn Val Glu Gln Asn Pro Ala Thr Ala Ala Val
                 405                 410                 415

Gly Gly Asn Lys Met Gly Arg Thr Thr Ser Met Gln Arg Val Ala Ser
             420                 425                 430

Leu Glu His Leu Gln Lys Arg Ile Arg Gly Glu Val Ser Ser Cys Gly
         435                 440                 445

Thr Gln Gly Arg Gly Glu Gln
    450                 455

<210> SEQ ID NO 6
<211> LENGTH: 442
<212> TYPE: PRT
<213> ORGANISM: Nicotiana tabacum

<400> SEQUENCE: 6

Met Asp Arg Val Phe Ser Val Asp Asp Ile Gly Asp His Phe Trp
1               5                   10                  15

Ser Thr Pro Pro Thr Ala Asp Leu Gly Val Asp Ser Pro Thr Thr Ala
             20                  25                  30

Thr Ala Ala Ser Tyr Ser Lys Met Met Asn Arg Ser Ser Glu Trp
         35                  40                  45

Ala Phe Gln Arg Phe Leu Gln Glu Ala Thr Ala Gly Thr Ser Thr
     50                  55                  60

Ser Ser His Pro Gln Pro Pro Thr Met Thr Ala Ser Ser Ser Ser Ser
65                  70                  75                  80

-continued

```
Ser His Gln Asn Asp Val Val Glu Ile Lys Asp Glu Asn Leu Ser Thr
                85                  90                  95

Pro Asn Leu Asn Pro Ser Thr Ala Leu Asn Ser Lys Pro Ala Ser Ser
               100                 105                 110

Phe Gly Leu Thr Pro Pro Pro Asn Ile Ala Val Asp Ser Glu Glu Tyr
               115                 120                 125

Gln Ala Phe Leu Lys Ser Gln Leu His Leu Ala Cys Ala Ala Val Ala
            130                 135                 140

Leu Thr Arg Gly Lys Ser Leu Asn Pro Gln Asp Ser Gly Ser Thr Ala
145                 150                 155                 160

His Asp Lys Gly Ser Glu Thr Ala Ser Ala Ala Gln Ser Gly Ser His
                165                 170                 175

Glu Met Ala Lys Ile Gln Asp Lys Asp Ala Gly Gly Pro Val Gly Ile
               180                 185                 190

Pro Ser Leu Pro Pro Val Gln Lys Lys Pro Val Val Gln Val Arg Ser
               195                 200                 205

Thr Thr Ser Gly Ser Ser Arg Glu Gln Ser Asp Asp Asp Glu Ala Glu
        210                 215                 220

Gly Glu Ala Glu Thr Thr Gln Gly Met Asp Pro Ala Asp Ala Lys Arg
225                 230                 235                 240

Val Arg Arg Met Leu Ser Asn Arg Glu Ser Ala Arg Arg Ser Arg Arg
                245                 250                 255

Arg Lys Gln Ala His Leu Thr Glu Leu Glu Thr Gln Val Ser Gln Leu
                260                 265                 270

Arg Val Glu Asn Ser Ser Leu Leu Lys Arg Leu Thr Asp Ile Ser Gln
            275                 280                 285

Lys Tyr Asn Glu Ala Ala Val Asp Asn Arg Val Leu Lys Ala Asp Val
        290                 295                 300

Glu Thr Leu Arg Ala Lys Val Lys Met Ala Glu Glu Thr Val Lys Arg
305                 310                 315                 320

Val Thr Gly Leu Asn Pro Leu Phe Gln Ala Met Ser Glu Ile Ser Ser
                325                 330                 335

Met Val Met Pro Ser Tyr Ser Gly Ser Pro Ser Asp Thr Ser Ala Asp
                340                 345                 350

Ala Ala Val Pro Val Gln Asp Asp Pro Lys His His Tyr Tyr Gln Gln
                355                 360                 365

Pro Pro Asn Asn His Met Pro Thr Asn Asp Pro Arg Ile Gln Asn Gly
370                 375                 380

Met Val Asp Val Pro Pro Ile Glu Asn Val Gln Gln Asn Pro Ala Thr
385                 390                 395                 400

Ala Ala Val Gly Gly Asn Lys Met Gly Arg Thr Ala Ser Met Gln Arg
                405                 410                 415

Val Ala Ser Leu Glu His Leu Gln Lys Arg Ile Arg Gly Glu Ile Ser
                420                 425                 430

Ser Cys Gly Thr Gln Gly Arg Gly Glu Gln
                435                 440
```

BZIP TRANSCRIPTION FACTORS REGULATE CONVERSION OF NICOTINE TO NORNICOTINE

RELATED APPLICATIONS

This application claims priority from International Patent Application No. PCT/US2018/064317, filed Dec. 6, 2018, which claims the benefit of U.S. Provisional Application Ser. No. 62/595,983, filed Dec. 7, 2017, the entire disclosures of which are incorporated herein by this reference.

SEQUENCE LISTING

The instant application contains a Sequence Listing which has been submitted in ASCII format via EFS-Web and is hereby incorporated by reference in its entirety. The ASCII copy of the Sequence Listing, which was created on Dec. 4, 2018, is named 13177N-2183US.txt and is 12 kilobytes in size.

TECHNICAL FIELD

The present invention relates to articles and methods for regulating conversion of nicotine to nornicotine. In particular, the presently-disclosed subject matter relates to transcription factors for regulating conversion of nicotine to nornicotine and methods of use thereof.

BACKGROUND

*Nicotiana tabacum* (common tobacco) is a natural allotetraploid originated about 200,000 years ago. The maternal S-genome is derived from ancestors of *N. sylvestris* and paternal T-genome from the relatives of *N. tomentosiformis*. Nicotine is the major alkaloid accumulated in most of the cultivated tobacco varieties. During the past decades, significant progress has been made in isolation and characterization structural genes in the nicotine biosynthetic pathway. Jasmonic acid (JA) is a major elicitor of nicotine biosynthesis. JAresponsive transcription factors (TFs) belong to two major families, APETALA2/ETHYLENE RESPONSE FACTORS (AP2/ERFs) and the basic HELIX-LOOP-HELIX (bHLH), and are known to induce the expression of genes encoding key enzymes in the nicotine biosynthetic pathway.

Nicotine and other tropane alkaloids, such as hyoscyamine and scopolamine, are synthesized in roots, and transported through xylem to the leaves. A number transporters have been isolated and characterized for their role in transport and vacuolar sequestration of alkaloids in plants. In tobacco, a number of transporters belonging to the MULTIDRUG and TOXIC COMPOUND ETRUSION (MATE) family, including MATE1/2 and Jasmonate-inducible Alkaloid Transporter (JAT1/2), are involved in transportation and vacuolar sequestration of nicotine. However, TFs involved in regulation of these transporter are not thoroughly studied.

In addition to nicotine, tobacco plants accumulate three other pyridine alkaloids namely, nornicotine, anabasine, and anatabine. Nornicotine is a demethylated nicotine (does not contain a methyl group) that is derived from nicotine by an enzymatic process. It is also a precursor to N-nitrosonornicotine (NNN), which is produced during the curing and processing of tobacco materials. More specifically, during post-harvest processing, nornicotine chemically reacts with the nitrosating agents to form NNN. As NNN belongs to a class of smoking related carcinogens called tobacco specific nitrosamines (TSNA), it is highly desirable to reduce TSNA in tobacco products.

There are two possible ways to reduce TSNA. One is to reduce overall nicotine content; the other is to eliminate conversion of nicotine to nornicotine. Conversion of nicotine to nornicotine is catalyzed by nicotine N-demethylase (NND), a small family of cytochrome P450 enzymes. Three NND genes, CYP82E4v1 (originated from *N. tomentosiformis*), CYP82E5v2 (originated from *N. tomentosiformis*), and CYP82E10 (originated from *N. sylvestris*), have been identified in the conversion of nicotine to nornicotine in tobacco. CYP82E4v1 (E4) plays a major role in nicotine to nornicotine conversion in senescent leaves, while expression of CYP82E10 (E10) is reported to be in the roots and CYP82E5 (E5) functions in both roots and leaves. However, up to this point, transcription factors (TFs) involved in the regulation of nicotine to nornicotine conversion (i.e., transcriptional regulators of E4, 5, and 10 genes) have not been identified. Therefore, although significant progress has been made in biochemical and molecular characterization of these nicotine transporters and enzymes involved in nornicotine biosynthesis, the molecular mechanism underlying the regulation of these genes remains to be elucidated.

Accordingly, there is a need for articles and methods that regulate the conversion of nicotine to nornicotine.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some embodiments, the presently-disclosed subject matter includes a method of decreasing conversion of nicotine to nornicotine, the method comprising administering at least one basic region/leucine zipper (bZIP) type transcription factor inhibitor to an organism in need thereof. In some embodiments, the at least one bZIP transcription factor inhibitor is selected from the group consisting of group C bZIP transcription factor inhibitors, group S bZIP transcription factor inhibitors, and combinations thereof. In some embodiments, the at least one bZIP transcription factor inhibitor is selected from the group consisting of an NtbZIP1a inhibitor, an NtbZIP1b inhibitor, an NtbZIP2a inhibitor, an NtbZIP2b inhibitor, and combinations thereof. In some embodiments, the at least one bZIP transcription factor inhibitor comprises an NtbZIP1a inhibitor and an NtbZIP1b inhibitor. In some embodiments, the at least one bZIP transcription factor inhibitor comprises an NtbZIP2a inhibitor and an NtbZIP2b inhibitor. In some embodiments, the at least one bZIP transcription factor inhibitor comprises an NtbZIP1a inhibitor, an NtbZIP1b inhibitor, an NtbZIP2a inhibitor, and an NtbZIP2b inhibitor.

In some embodiments, the at least one bZIP transcription factor inhibitor is selected from the group consisting of antisense oligonucleotides, miRNA, siRNA, locked nucleic acid (LNA) nucleotides, and combination thereof. In one embodiment, the at least one bZIP transcription factor inhibitor comprises an antisense oligonucleotide of a bZIP transcription factor selected from the group consisting of NtbZIP1a, NtbZIP1b, NtbZIP2a, NtbZIP2b, and combinations thereof.

Also provided herein, in some embodiments, is a method of decreasing conversion of nicotine to nornicotine, the method comprising mutating a basic region/leucine zipper (bZIP) type transcription factor binding site on a promoter of a nicotine N-demethylase (NND). In some embodiments, the NND is selected from the group consisting of CYP82E4v1, CYP82E5v2, and CYP82E10. In one embodiment, the NND is CYP82E4v1. In another embodiment, the bZIP binding site on the promoter of CYP82E4v1 is an A/G box with a pre-mutated sequence of TACGTC. In a further embodiment, the mutated binding site has the sequence TGCGTC. In some embodiments, the mutated binding site is formed by site-directed mutagenesis. In some embodiments, the method also includes administering at least one bZIP type transcription factor inhibitor to an organism in need thereof. In one embodiment, the at least one bZIP transcription factor inhibitor is selected from the group consisting of an NtbZIP1a inhibitor, an NtbZIP1b inhibitor, an NtbZIP2a inhibitor, an NtbZIP2b inhibitor, and combinations thereof.

Further provided herein, in some embodiments, is a method of decreasing conversion of nicotine to nornicotine, the method comprising mutating a plant genome to knockout at least one basic region/leucine zipper (bZIP) type transcription factor. In some embodiments, the at least one bZIP transcription factor is selected from the group consisting of group C bZIP transcription factor, group S bZIP transcription factor, and combinations thereof. In some embodiments, the at least one bZIP transcription factor is selected from the group consisting of NtbZIP1a, NtbZIP1b, NtbZIP2a, NtbZIP2b, and combinations thereof. In some embodiments, the at least one bZIP transcription factor is selected from the group consisting of NtbZIP1a and NtbZIP2a, NtbZIP1b and NtbZIP2b, and combinations thereof. In some embodiments, the method also includes administering at least one bZIP type transcription factor inhibitor to an organism in need thereof. In one embodiment, the at least one bZIP transcription factor inhibitor is selected from the group consisting of an NtbZIP1a inhibitor, an NtbZIP1b inhibitor, an NtbZIP2a inhibitor, an NtbZIP2b inhibitor, and combinations thereof.

Further features and advantages of the presently-disclosed subject matter will become evident to those of ordinary skill in the art after a study of the description, figures, and non-limiting examples in this document.

BRIEF DESCRIPTION OF THE DRAWINGS

The presently-disclosed subject matter will be better understood, and features, aspects and advantages other than those set forth above will become apparent when consideration is given to the following detailed description thereof. Such detailed description makes reference to the following drawings, wherein:

FIG. 6 shows an image comparing the nucleotide and amino acid sequences of NtbZIP1a (SEQ ID NOS: 1 and 2) and NtbZIP1b (SEQ ID NOS: 3 and 4).

Figure 1:
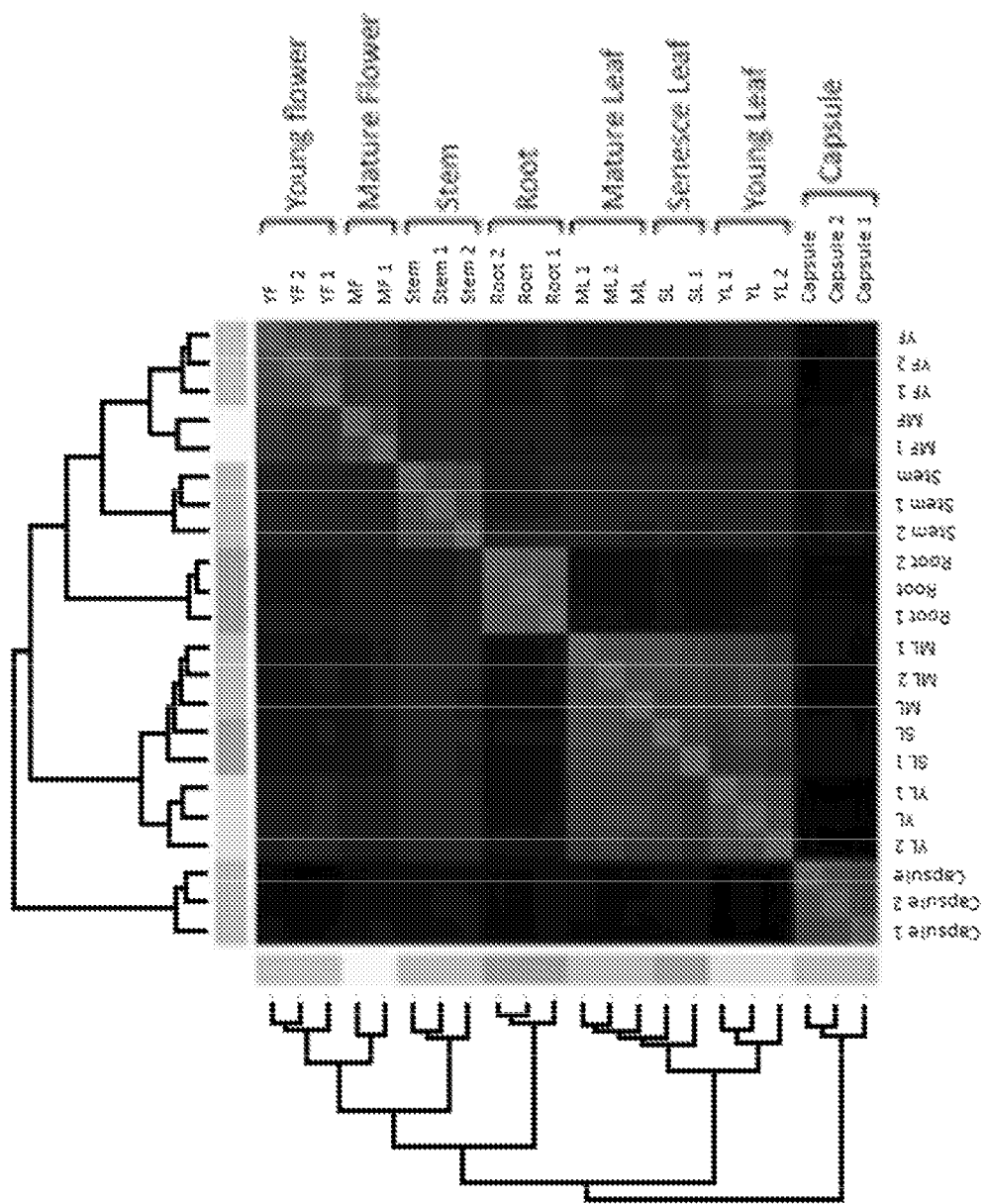
FIG. 1 shows a graph illustrating hierarchical cluster analysis of the transcriptome data of eight different tobacco tissues. Each tissue forms a distinct cluster based on the expression.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

Definitions

Unless defined otherwise, all technical and scientific terms used herein have the same meaning as commonly understood by one of ordinary skill in the art to which the disclosure belongs. Any methods and materials similar to or equivalent to those described herein can be used in the practice or testing of the present disclosure, including the methods and materials are described below.

Following long-standing patent law convention, the terms "a," "an," and "the" refer to "one or more" when used in this application, including the claims. Thus, for example, reference to "a cell" includes a plurality of cells, and so forth.

The terms "comprising," "including," and "having" are intended to be inclusive and mean that there may be additional elements other than the listed elements.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration, percentage, or the like is meant to encompass variations of in some embodiments ±50%, in some embodiments ±40%, in some embodiments ±30%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

All combinations of method or process steps as used herein can be performed in any order, unless otherwise specified or clearly implied to the contrary by the context in which the referenced combination is made.

DETAILED DESCRIPTION

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

The presently-disclosed subject matter relates to articles and methods for regulating conversion of nicotine to nornicotine. In some embodiments, the article includes one or more transcription factor (TF) inhibitors. In one embodiment, for example, the article includes one or more inhibitors of basic region/leucine zipper (bZIP) type transcription factors. In another embodiment, the bZIP type transcription factors are derived from tobacco. In a further embodiment, of the 133 bZIP type transcription factors identified in tobacco by the instant inventors, which are classified into ten sub-groups: A, B, C, D, E, F, G, H, and S, suitable bZIP type transcription factors include at least one of the 27 bZIPs in sub-group S, at least one of the 6 bZIPs in sub-group C, other bZIP 63 homologs, or a combination thereof. In certain embodiments, the S sub-group bZIP transcription factor includes, but is not limited to, NtbZIP1a (SEQ ID NOs: 1 and 2), NtbZIP1b (SEQ ID NOs: 3 and 4), or a combination thereof; and/or the C sub-group bZIP transcription factor includes, but is not limited to, NtbZIP2a (SEQ ID NO: 5), NtbZIP2b (SEQ ID NO: 6), or a combination thereof.

The one or more transcription factor inhibitors include, but are not limited to, antisense oligonucleotides, miRNA, siRNA, locked nucleic acid (LNA) nucleotides, or a combination thereof. In some embodiments, the inhibitors provide RNAi-mediated knock-down/silencing of the bZIP type transcription factors. As will be appreciated by those skilled in the art, the specific sequence/structure of the transcription factor inhibitors is based upon the sequence of the specific transcription factor. Accordingly, as will also be appreciated by those skilled in the art, the antisense oligonucleotides and/or LNAs may be formed by any suitable method using the bZIP type transcription factor sequences provided herein. For example, in one embodiment, the inhibitor includes an antisense oligonucleotide having 100% sequence homology with the complementary bZIP type transcription factor. In another embodiment, the transcription factor inhibitor includes an antisense oligonucleotide having 100% sequence homology with a bZIP type transcription factor complementary to NtbZIP1a, NtbZIP1b, NtbZIP2a, and/or NtbZIP2b. In such embodiments, the transcription factor inhibitor(s) provide RNAi-mediated knock-down/silencing of NtbZIP1a, NtbZIP1b, NtbZIP2a, and/or NtbZIP2b expression in tobacco.

Also provided herein, in some embodiments, is a method of regulating the conversion of nicotine to nornicotine in a tobacco plant or other nicotine containing organism. In one embodiment, the method includes administering one or more of the bZIP inhibitors disclosed herein to a nicotine containing organism. Administration of these one or more bZIP inhibitors decreases or eliminates conversion of the nicotine to nornicotine. The one or more inhibitors may be administered for a single type of bZIP transcription factor, or for a combination of bZIP transcription factors. For example, in one embodiment, the method includes administering one or more inhibitors for S bZIP type transcription factors or C bZIP type transcription factors. In another embodiment, the method includes administering one or more inhibitors for S bZIP type transcription factors and one or more transcription factors for C bZIP type transcription factors. In a further embodiment, the method includes administering one or more inhibitors of NtbZIP1a, NtbZIP1b, NtbZIP2a, and/or NtbZIP2b to the organism. In certain embodiments, inhibiting both S bZIP type transcription factors and C bZIP type transcription factors has a synergistic effect on the reduction or elimination of nicotine conversion to nornicotine.

The methods disclosed herein include administering a single type of inhibitor or any suitable combination of inhibitors, which may be the same or different for each bZIP transcription factor being inhibited. For example, in one embodiment, the method includes administering antisense oligonucleotides of NtbZIP1a, NtbZIP1b, NtbZIP2a, and/or NtbZIP2b. In another embodiment, the method includes administering antisense oligonucleotides of one bZIP transcription factor, such as NtbZIP1a, and LNA nucleotides of another bZIP transcription factor, such as NtbZIP1b. As will be appreciated by those skilled in the art, although discussed above with regard to certain combinations of bZIP transcription factors and transcription factor inhibitors, the disclosure is not so limited and may include any other suitable combination of TFs and TF inhibitors.

Additionally or alternatively, the method may include bZIP type transcription factor knockout and/or mutation of a bZIP type transcription factor binding site on the promoter of the nicotine N-demethylase (NND). For example, in one embodiment, the method includes editing the plant genome to knock-out NtbZIP1a, NtbZIP1b, NtbZIP2a, and/or NtbZIP2b. The genome editing may be performed through any suitable process, such as, but not limited to, CRISPR/Cas9-mediated genome editing. In another embodiment, the method includes mutating the bZIP binding element in the E4 promoter, called A/G box (TACGTC), to TGCGTC by site-directed mutagenesis. Although discussed above with regard to a specific mutation in the E4 promoter, as will be appreciated by those skilled in the art, the disclosure is not so limited and includes any other mutation in the E4, E5, and/or E10 promoter to reduce or eliminate activation of the respective NND by the bZIP type transcription factor.

The administration of the TF inhibitors, the TF knockout, and/or the binding site mutation disclosed herein reduces or eliminates activation of the NND by the bZIP type transcription factor, which decreases or eliminates conversion of nicotine to nornicotine. As opposed to existing articles that include E4, E5, and E10 mutants, the articles disclosed herein control the expression of E4, E5, and E10 to reduce or eliminate the conversion of nicotine to nornicotine. By reducing or eliminating the conversion of nicotine to nornicotine the articles and methods disclosed herein decrease the harmful effects of products which typically contain the carcinogenic nornicotine, such as, but not limited to, tobacco products.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

Figure 2:
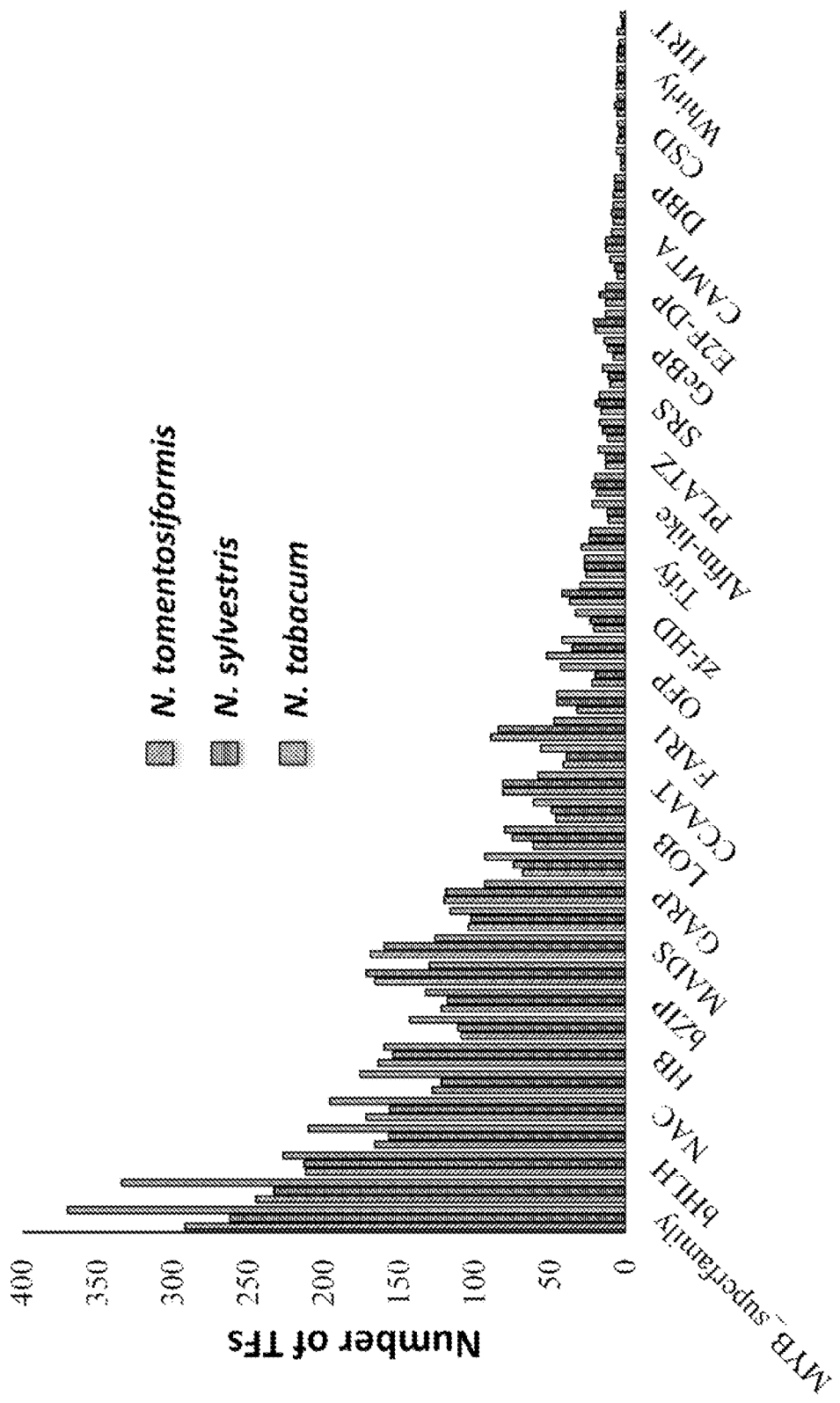
FIG. 2 shows a graph illustrating distribution of different TF families in tobacco and its progenitors.
Figure 3:
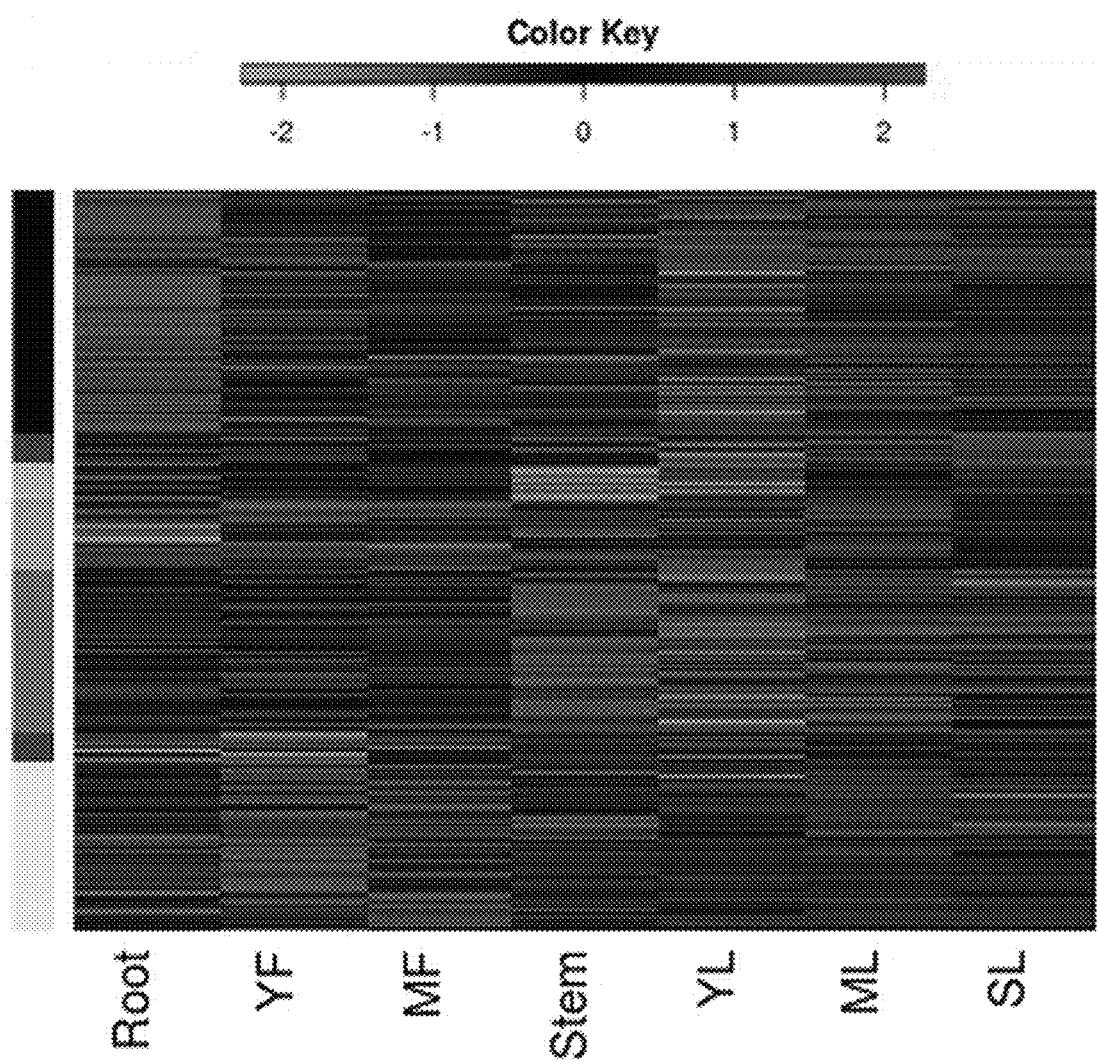
FIG. 3 shows a graph illustrating co-expression analysis of TF genes, and structural genes in nicotine biosynthetic pathway in different tissue. The TF and structural genes are grouped into 8 different modules (color-coded side bar) based on their expression. The black module contains majority of the structural gene nicotine biosynthetic pathway. YF, young flower; MF, mature flower; YL, young leaf; ML, mature leaf SL, senesce leaf.

This Example describes the analysis of transcriptome data sets of different tobacco tissues, including leaf (young, mature, and senesce leaf), root, stem, flower (young and mature flower), and capsule to generate a co-expression network. First, a hierarchical cluster analysis was performed, which revealed that each individual tissue type exhibits a unique expression pattern (FIG. 1). Next, the genes encoding all major TF families in tobacco and its progenitors were identified. The tobacco genome contains more TF genes than its progenitors and the number of TFs belonging to MYB, AP2/ERFs, and bHLH families are significantly higher than other families (FIG. 2). In view thereof, the TFs and structural genes in the nicotine biosynthetic pathway were then grouped into 8 different modules (color-coded side bar) based on their expression pattern in different tissues (FIG. 3). The "black" module is particularly interesting as majority of the nicotine biosynthetic genes were found in this module along with a number of TF genes. Many of these TFs belong to MYB, bHLH, bZIP, and ERF families. As discussed in Examples 2-4 below, the role of these TFs in nicotine biosynthesis in tobacco is established through isolation and functional characterization thereof.

Example 2

This Example describes two bZIP type transcription factors from tobacco (FIG. 4), which regulate the conversion of nicotine to nornicotine, can be used for reduction of smoking related carcinogen, tobacco specific nitrosamines (TSNA).

bZIP TFs are characterized by a conserved leucine zipper motif that mediates dimer formation for DNA binding. In plants, bZIP TFs regulate processes including pathogen defense, light and stress signaling, seed maturation, and flower development. Many bZIP factors, especially those in tobacco, are not well characterized. By co-expression and clustering analyses, two bZIP TF genes that co-express with E4, E5, and E10 were identified herein. These tobacco bZIP TFs have been termed NtbZIP1a and NtbZIP1b.

Figure 4:
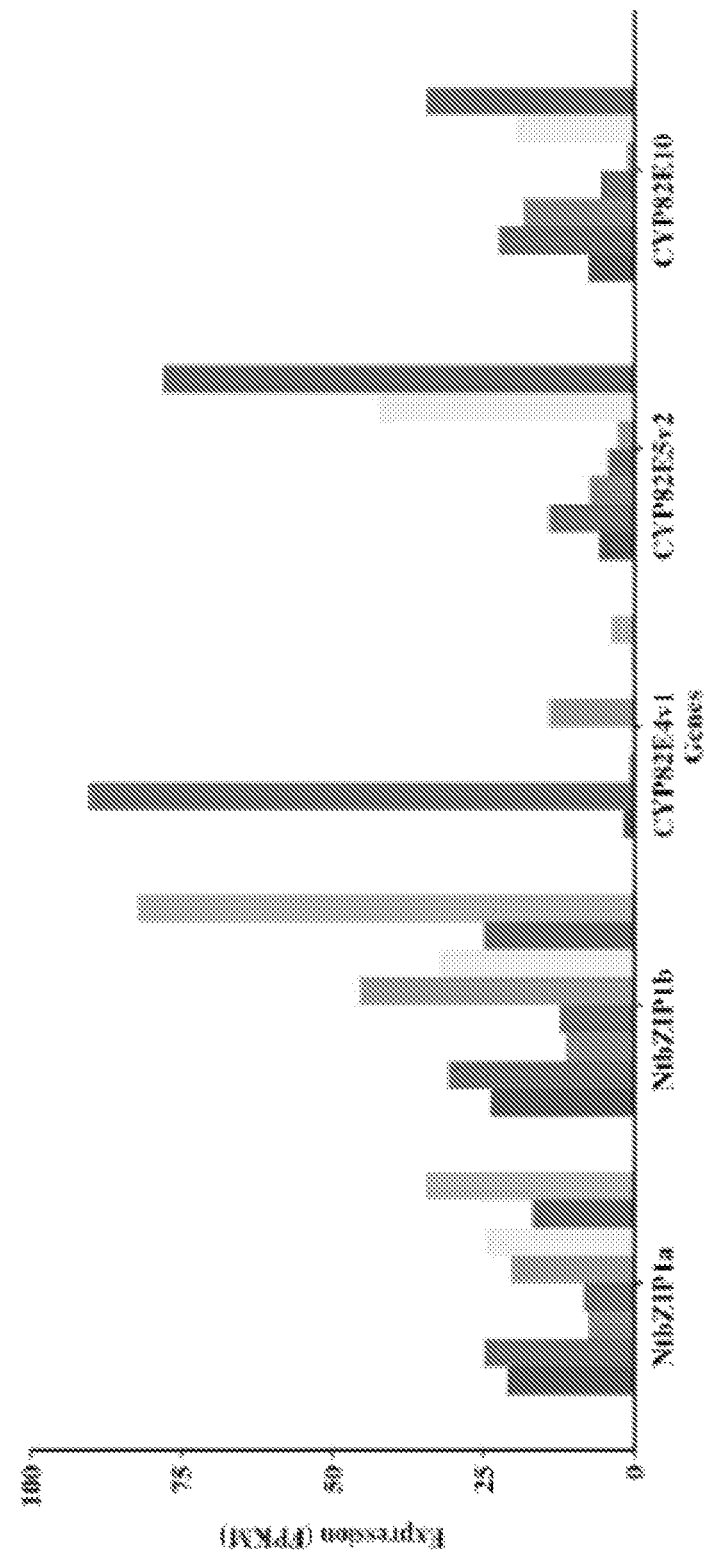
FIG. 4 shows a graph illustrating expression of NtbZIP1a/b and NNDs in different tobacco tissues.
Figure 5:
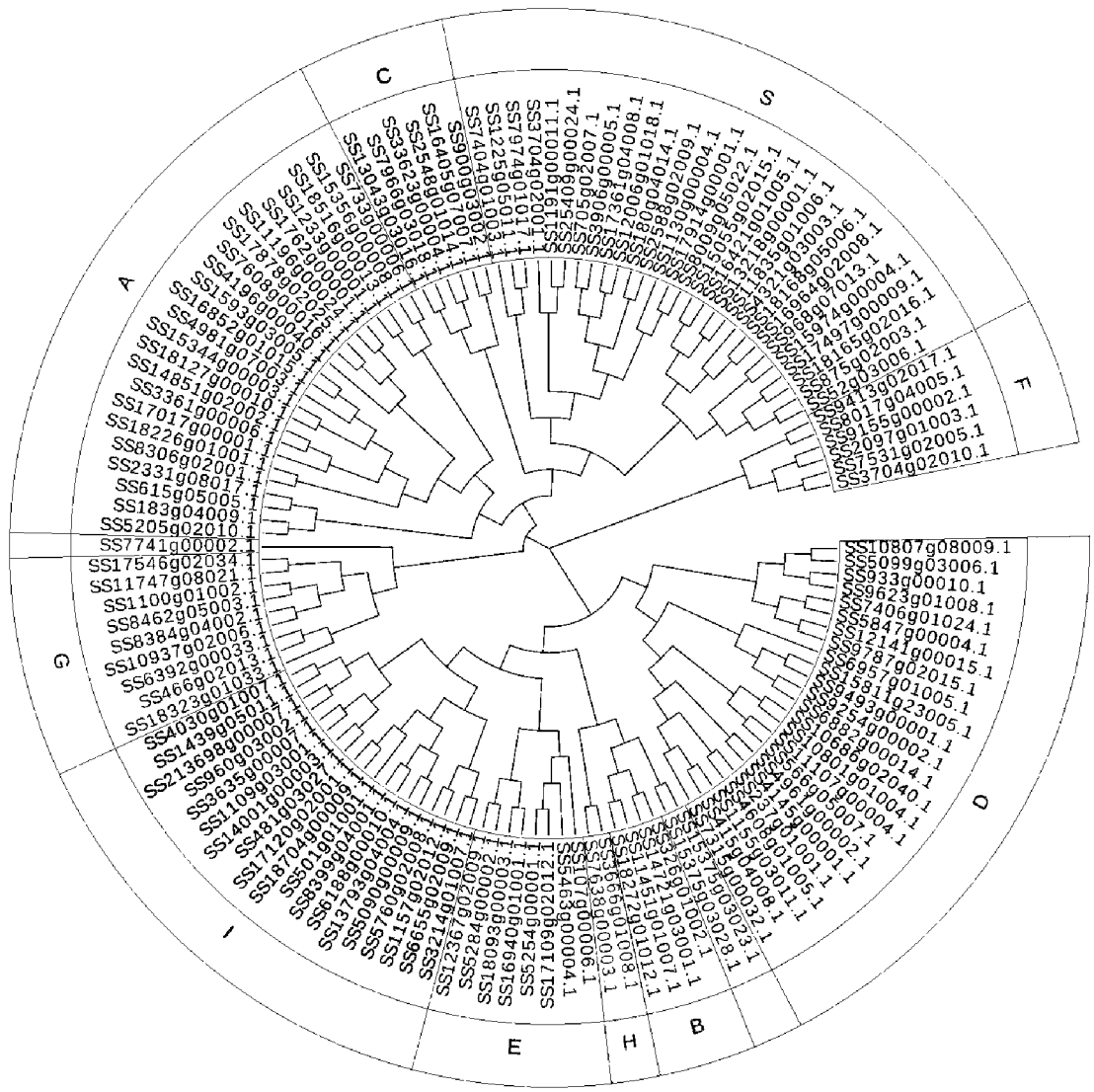
FIG. 5 shows an image illustrating the bZIP family in tobacco. NtbZIP1a and NtbZIP1b are indicated by *.
Figure 6:
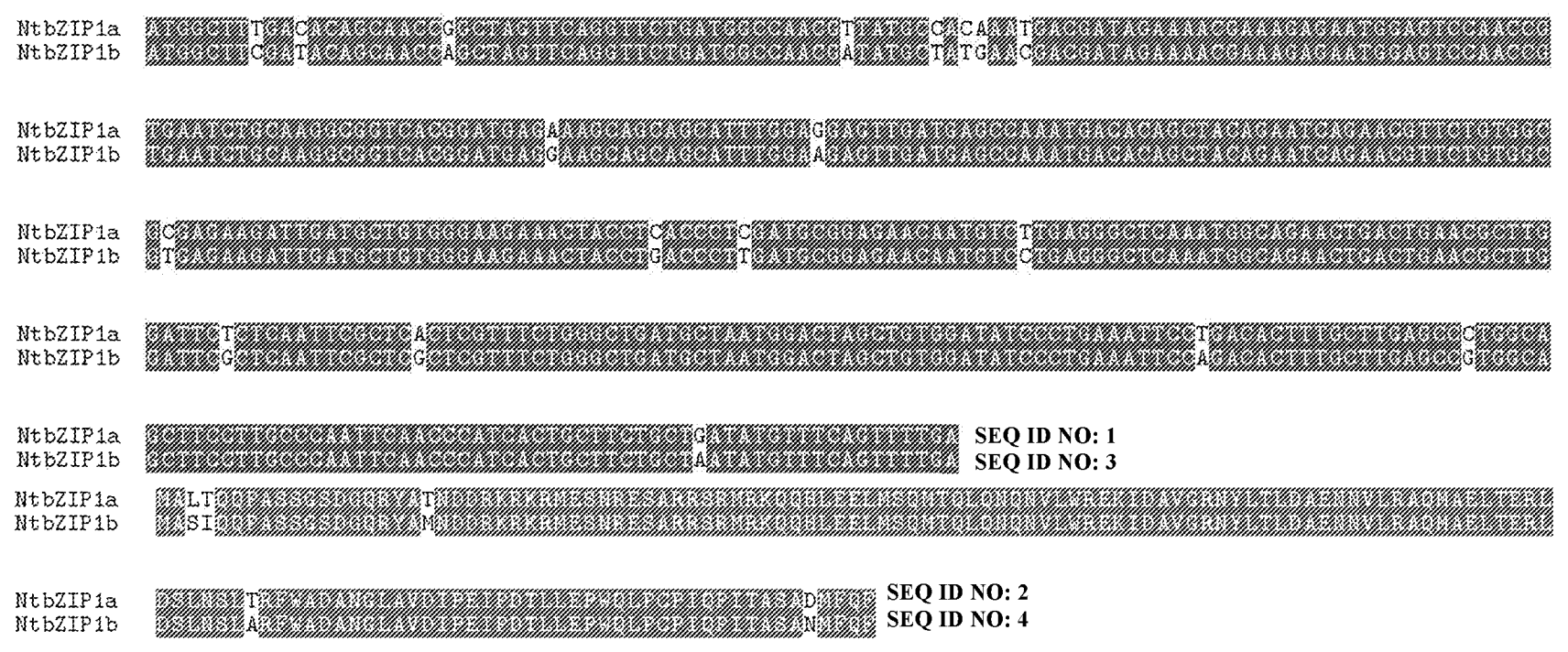

NtbZIP1a/b exhibit similar expression patterns as compared to CYP82E4v1, the major NND enzyme involved in nicotine to nornicotine conversion, and are highly expressed in flowers and senescent leaves (FIG. 4). As illustrated in FIG. 5, 133 bZIPs were identified in tobacco and classified into ten sub-groups: A, B, C, D, E, F, G, H, I, and S, with NtbZIP1 a/b belonging to sub-group S. In maize, expression of group-S bZIPs are induced by wounding, cold, and drought stress. Referring to FIG. 6, it was also found that NtbZIP1a and b are more than 97% identical at nucleotide and amino acid level. Without wishing to be bound by theory, it is believed that the two homologous bZIPs are derived from two progenitors of tobacco, *N. sylvestris* and *N. tometosiformis*.

Figure 7:
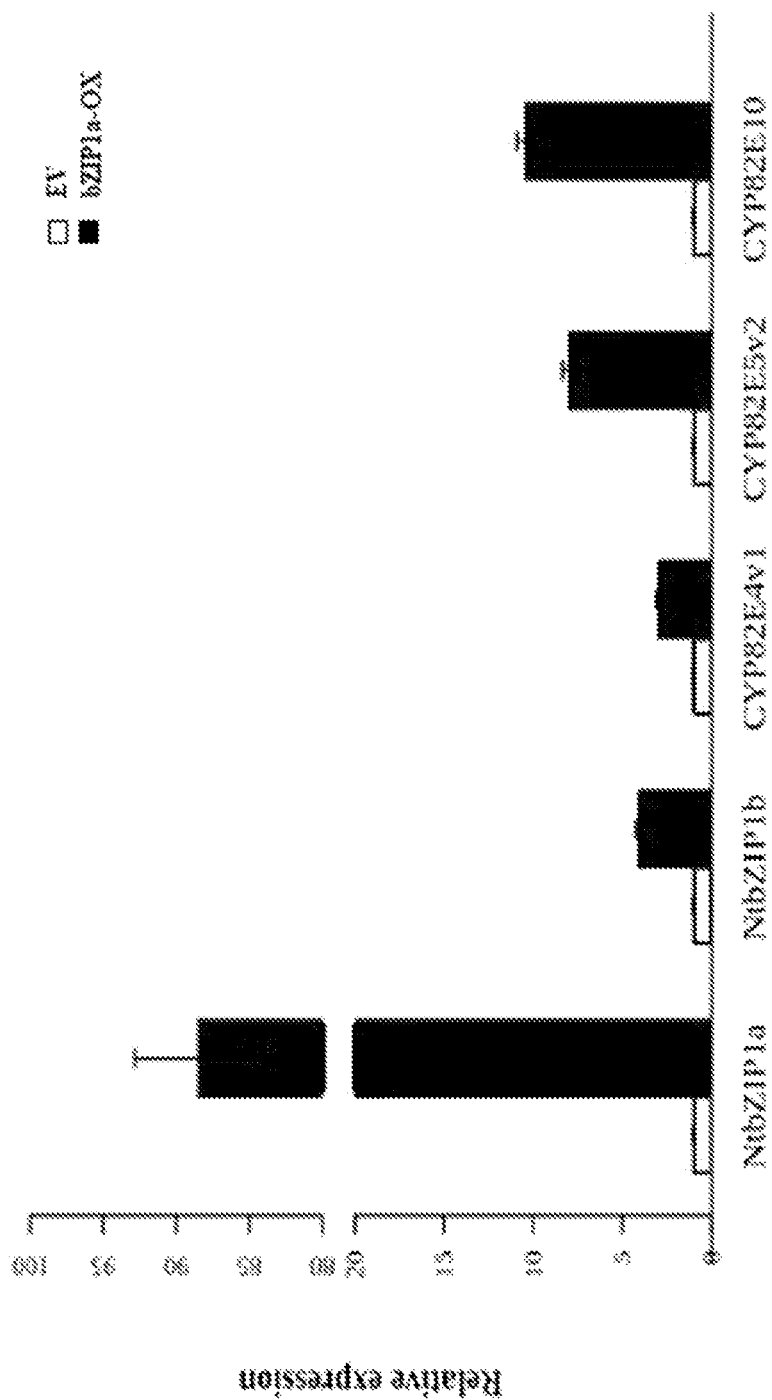
FIG. 7 shows a graph illustrating that transient overexpression of NtbZIP1a in tobacco leaves induces the expression of CYP82E4v1, CYP82E5v2, and CYP82E10.

After identifying the two bZIP TFs, whether overexpression of NtbZIP1a leads to upregulation of E4, 5, and 10 was tested. NtbZIP1a was cloned into pCAMBIA2300 (binary vector) under the control of the CaMV 35S promoter and rbcS terminator. The binary vectors (empty control and NtbZIP1a) were mobilized into *Agrobacterium*, and tobacco leaves were infiltrated using the transformed *Agrobacterium*. Total RNA isolated from *Agrobacterium*-infiltrated leaf discs were used for cDNA synthesis and real-time quantitative PCR (qRT-PCR) was used to detect the transcript levels of NtbZIP1a, NtbZIP1b, E4, 5, and 10. An ubiquitously expressed house-keeping gene, tubulin, was used as internal control in qRT-PCR. The results showed that, when NtbZIP1a was highly expressed transiently, the endogenous NtbZIP1b, E4, 5, and 10 were upregulated (approx. 3-10 fold), indicating that NtbZIP1a induces the expression of NtbZIP1b, E4, 5, and 10, hence a possible transcriptional activator for these genes (FIG. 7).

Figure 8:
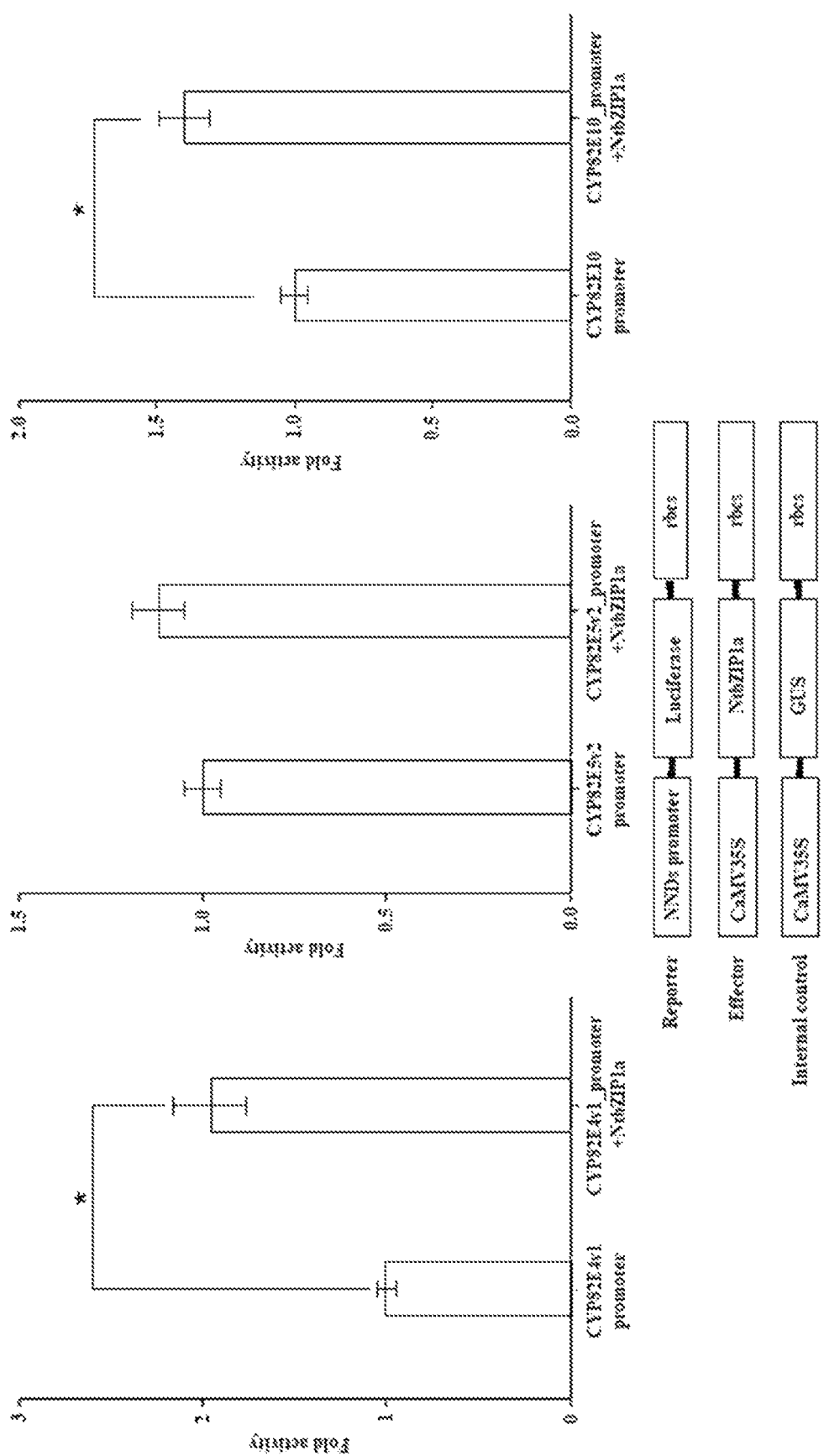
FIG. 8 shows a graph illustrating that NtbZIP1a significantly activates CYP82E4v1 and CYP82E10 promoters in tobacco cells.

Next, whether NtbZIP1a can bind to the promoters of its potential target genes was tested. The promoters (approximately 1.0 kb fragment of the 5' untranslated region of each coding gene) of E4, 5, and 10 were isolated, and the individual promoters were fused to a firefly luciferase reporter gene. The NtbZIP1a gene was cloned into the pBlueScript (pBS) vector under the control of the CaMV 35S promoter and rbcS terminator. The plasmids were electroporated into tobacco protoplasts. NtbZIP1a significantly induced the luciferase gene expression controlled by the E4 and E10 promoters, but not E5 promoter, suggesting that NtbZIP1a can directly activate E4 and E10 genes, likely by binding to their promoters (FIG. 8). NtbZIP1a did not appear to bind to the 1.0 kb promoter region of E5, used for the activation experiment. However, as mentioned above, overexpression of NtbZIP1a led to upregulation of E5, together with E4 and 10. The promoter activation experiment indicates two possible NtbZIP1a regulatory relationships with E5 gene: (1) NtbZIP1a binds to a site outside of the 1.0 kb promoter fragment, or (2) NtbZIP1a indirectly activates E5, through another unidentified activator in tobacco (e.g., NtbZIP1a activates another activator, which in turn activates E5).

Figure 9:
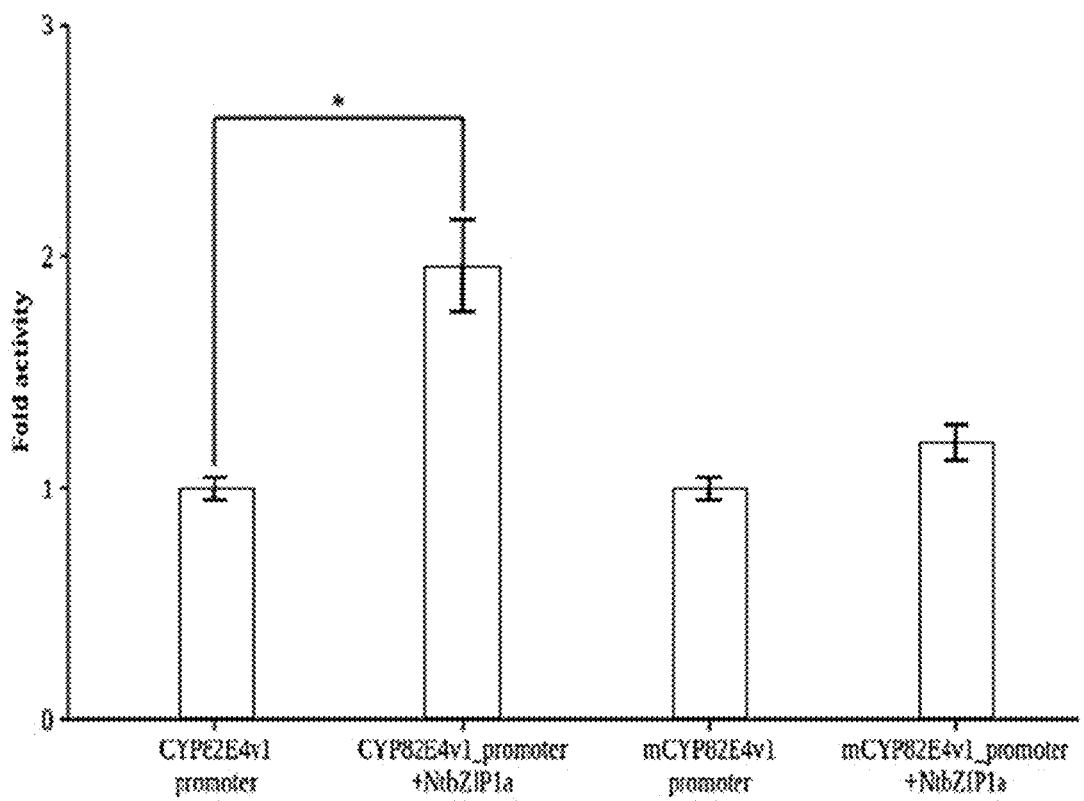
FIG. 9 shows a graph illustrating that NtbZIP1a activates CYP82E4v1 promoter in tobacco cells by binding to the A/G box.
Figure 9:
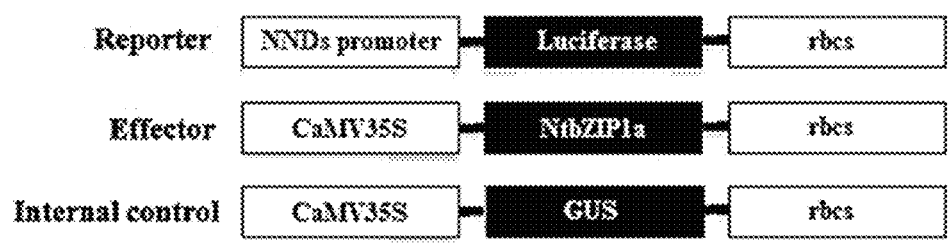

To support the possibility of NtbZIP1a directly binding to the E4 promoter to regulate transactivation the bZIP binding element in the E4 promoter, called A/G box (TACGTC), was mutated to TGCGTC by site-directed mutagenesis. The mutated promoter was fused to the luciferase reporter gene as described above. A transactivation experiment was then performed using the mutant reporter plasmid and the NtbZIP1a expression vector, as described above. The result showed that NtbZIP1a is unable to activate the luciferase gene expression under the control of the mutant promoter (FIG. 9). This experiment demonstrated that the E4 promoter is activated through an A/G-box binding factor, most likely NtbZIP1a.

Figure 10:
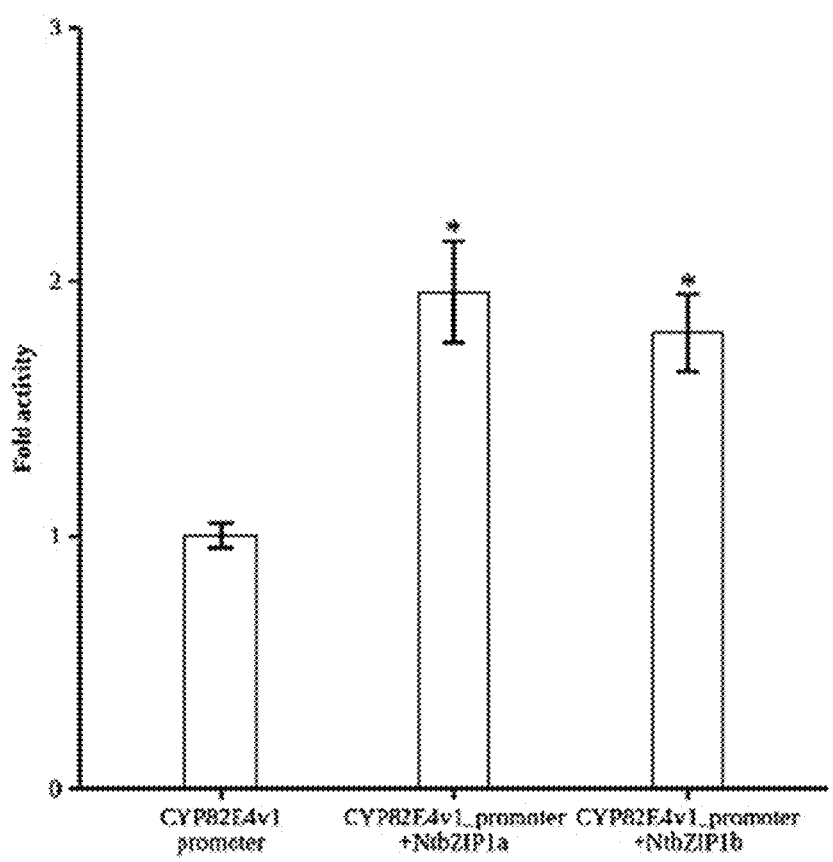
FIG. 10 shows a graph illustrating that NtbZIP1a and b significantly activate CYP82E4v1 promoter in tobacco cells.
Figure 10:
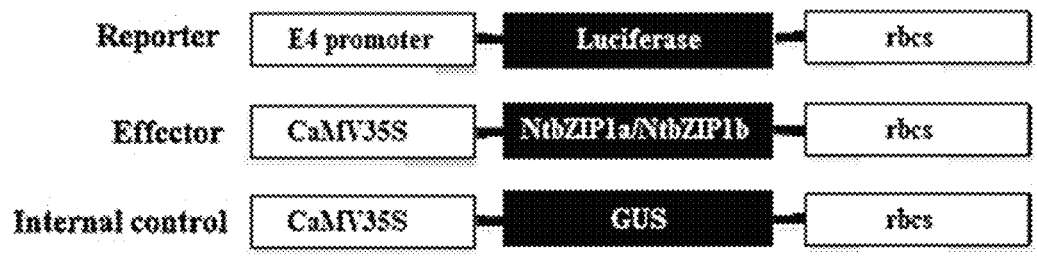

Referring to FIG. 10, the transactivation experiment was also performed using a NtbZIP1b expression vector and the E4 promoter-luciferase reporter plasmid, as described for NtbZIP1a. NtbZIP1b also activated the E4 promoter at the similar level as NtbZIP1a.

Figure 11:
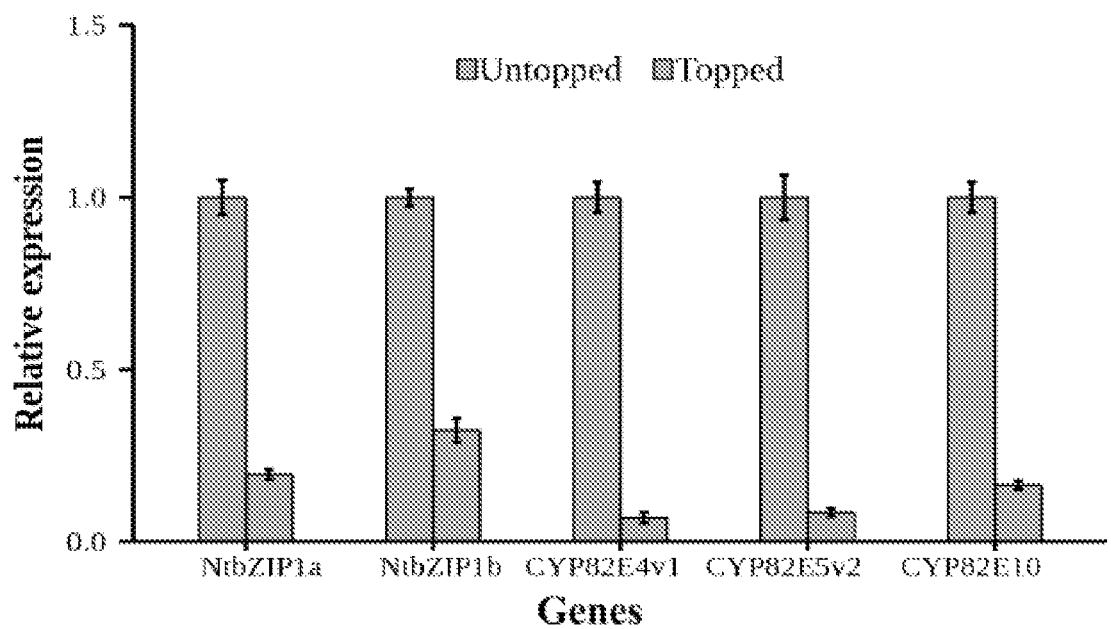
FIG. 11 shows a graph illustrating that topping of tobacco plants downregulates the expression of NtbZIPs and NNDs.

Finally, as it has been established that the agronomic practice of tobacco topping (removal of the axillary shoots) induces nicotine production, the instant inventors analyzed the transcriptome data from tobacco plants that were topped or un-topped. More specifically, leaf samples were collected after 24 hours from the control (un-topped) and topped plants. RNA isolated from un-topped and topped leaves were used for cDNA synthesis and qRT-PCR analyses. The results showed that topping resulted in decreased expression of bZIP1a/b, as well as E4, 5, and 10, by approximately 70-90%, compared to the un-topped plants, suggesting that topping negatively regulates the expression of bZIP1a/b and NNDs in tobacco (FIG. 11). The result also indicates that bZIP1a/b and NNDs are coordinately expressed in tobacco, as gene regulators and their target genes usually do.

Based upon the Example above, NtbZIP1a and 1b are believed to be involved in the regulation of the three NND genes as activators. Reduction or inactivation of NtbZIP1a/b may lead to reduction of nornicotine.

Example 3

This Example describes the formation of transgenic lines overexpressing NtbZIP1a and the effect of these transgenic lines on endogenous E4 expression.

Figure 12A:
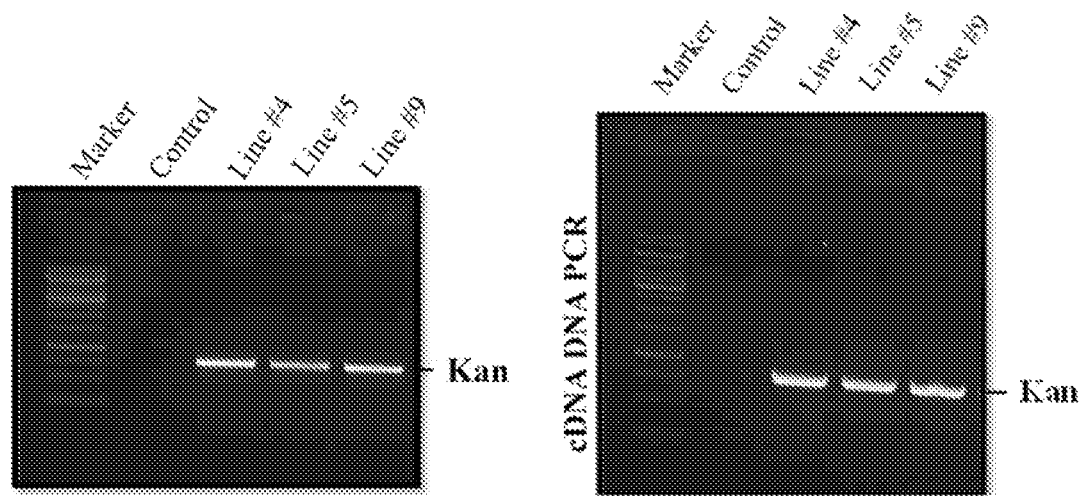
FIGS. 12A-C show graphs and images illustrating overexpression of NtbZIP1a in tobacco plants. (A) Genomic DNA PCR and cDNA PCR of control and three transgenic lines (line #4, 5, and 9) confirming the integration and expression, respectively, of the antibiotic selection marker, neomycin phosphotransferase II (npt II; Kan). (B) Quantitative real-time (qRT-PCR) analysis showing the relative expression of NtbZIP1 and E4 in control (EV) and transgenic lines (line #4, 5, and 9). (C) Metabolic analysis showing conversion of nicotine to nornicotine in control and transgenic lines (To or first generation transgenic plants).
Figure 12B:
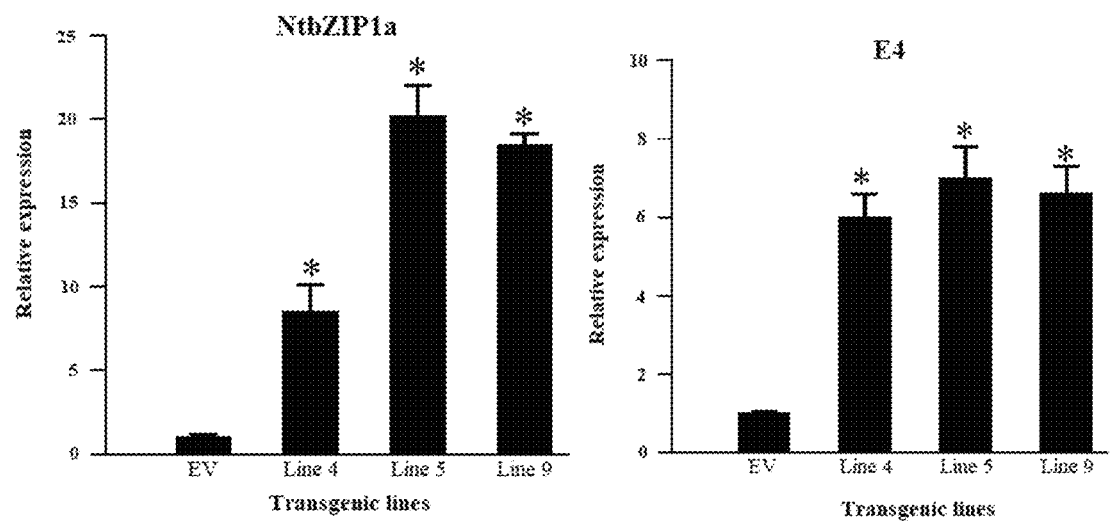

To form the transgenic lines, the pCAMBIA2300 (binary vector), containing NtbZIP1a under the control of the CaMV 35S promoter and rbcS terminator, was mobilized into *Agrobacterium*, and tobacco leaf discs were infected with the transformed *Agrobacterium*. More than 20 transgenic lines overexpressing NtbZIP1a were generated from *Agrobacterium*-infected leaf discs. Genomic DNA isolated from control and three transgenic lines were used to verify the transgenic status of the plants by PCR amplification of the antibiotic selection marker, neomycin phophotransferase II (nptII; kan). Total RNA isolated from leaves of control and three transgenic lines were used for cDNA synthesis. RT-PCR was used to verify the expression of nptII (kan) gene in the transgenic plants (FIG. 12A). Real-time quantitative PCR (qRT-PCR) was used to detect the transcript levels of NtbZIP1a, and E4 (FIG. 12B). An ubiquitously expressed house-keeping gene, tubulin, was used as internal control in qRT-PCR.

Figure 12C:
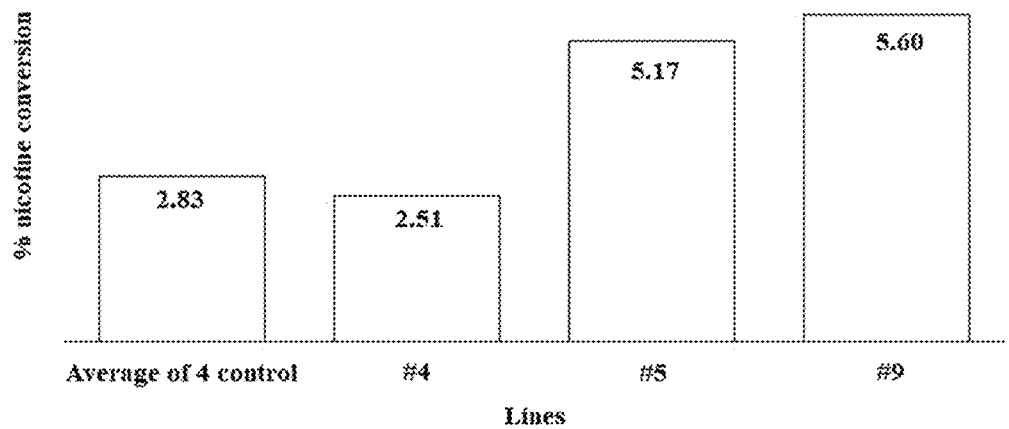

The results of this Example showed that NtbZIP1a expression was significantly higher in the transgenic plants compared with control. When NtbZIP1a was highly expressed the endogenous E4 expression was unregulated (approx. 6-8 fold), indicating that NtbZIP1a induces the expression of E4 and therefore is a possible transcriptional activator for E4 gene. Additionally, metabolic analysis shows that nicotine to nornicotine conversion is higher in transgenic tobacco leaves as compared with a control (FIG. 12C). The formula used for calculating the conversion of nicotine to nornicotine was:

$$\text{Nicotine conversion} = \frac{\text{Nornicotine}}{\text{Nicotine} + \text{Nornicotine}} \times 100$$

Two of the three lines analyzes showed higher nicotine to nornicotine conversion. Because the metabolic analysis was performed with independent $T_0$ (first generation transgenic plants) segregating population, the metabolic outcomes can vary.

Example 4

Figure 13:
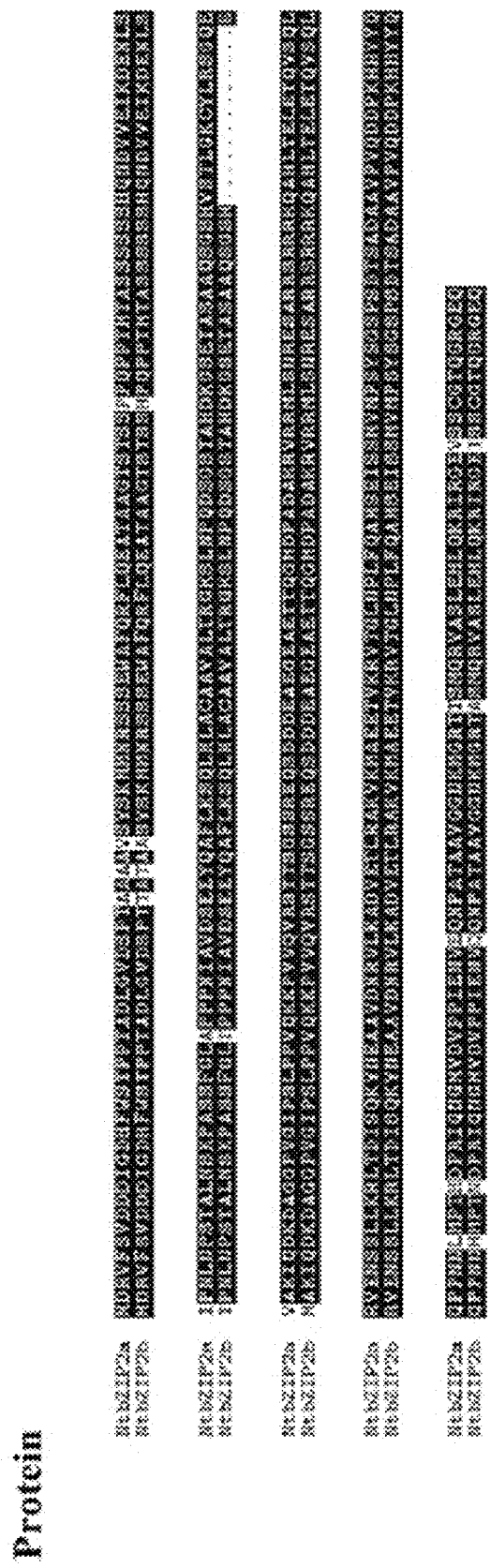
FIG. 13 shows an image illustrating amino acid sequence alignment of NtbZIP2a and 2b.

As described in Example 2 above, the instant inventors have characterized NtbZIP1a and b, two NtbZIP belonging to group S bZIP factors. In *Arabidopsis*, group S bZIP factors are known to interact with certain group C factors to regulate gene expression. In view of this interaction, the instant inventors identified the tobacco homologs of *Arabidopsis* bZIP 63, a group C member that interacts with group S factors. In tobacco, there are two bZIP 63 homologs, termed here as NtbZIP2a and b, that share greater than 95% in amino acid identity (FIG. 13). Without wishing to be bound by theory, it is believed that NtbZIP2a and b are originated from the two tobacco progenitors, *N. sylvestris* and *N. tometosiformis*, and functionally redundant.

Figure 14:
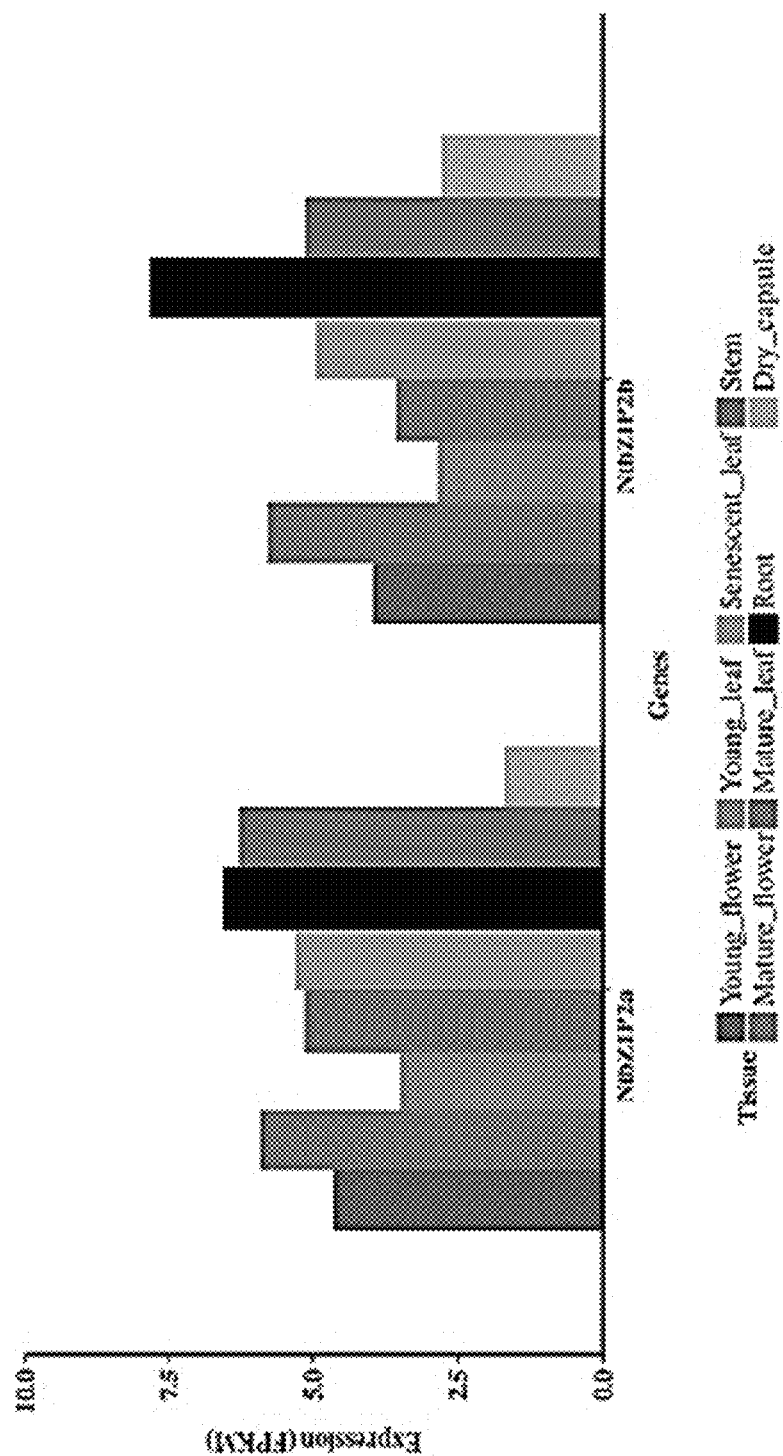
FIG. 14 shows a graph illustrating that NtbZIP2a and b have similar expression patterns in tobacco tissues.
Figure 15:
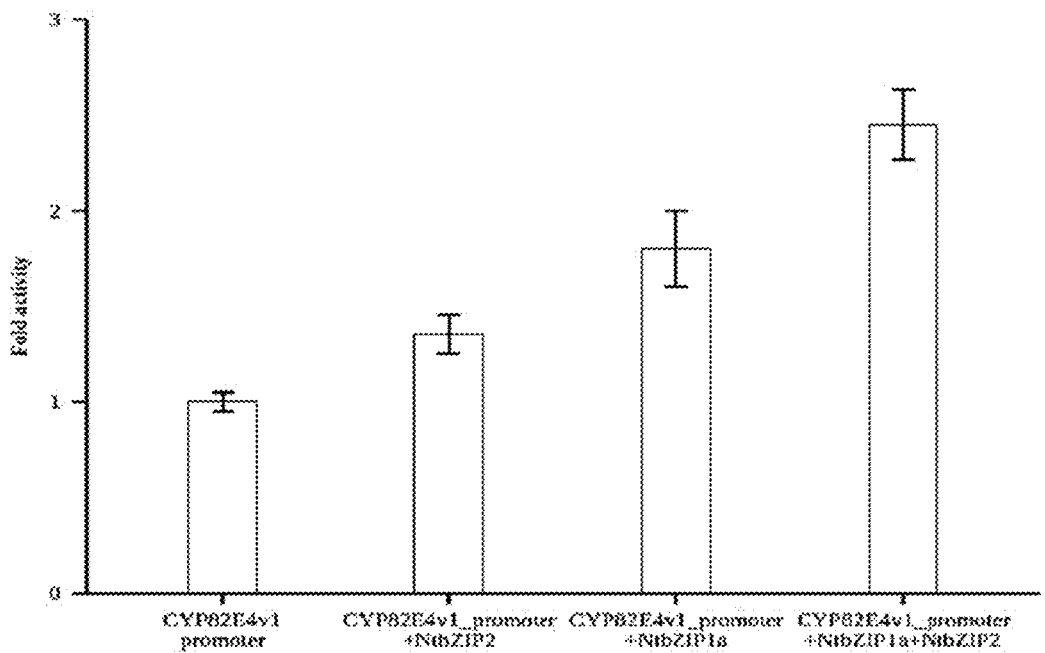
FIG. 15 shows a graph illustrating that NtbZIP2 acts synergistically with NtbZIP1 to activate the E4 promoter in tobacco cells.
Figure 15:
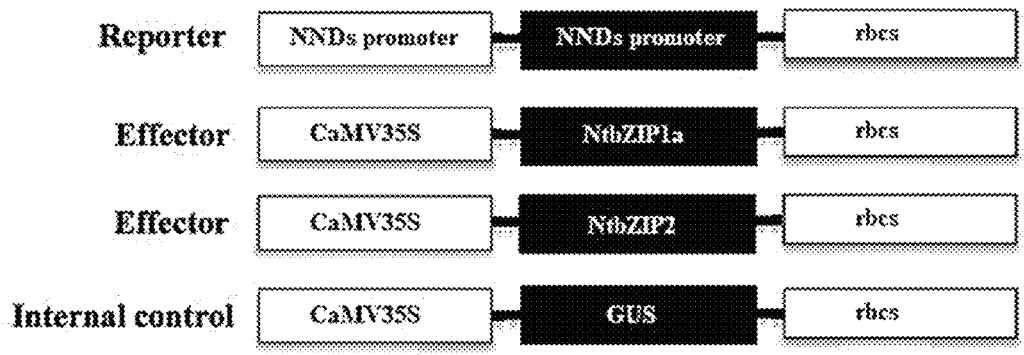

According to transcriptomic analysis, NtbZIP2a and b have similar expression patterns in tobacco flowers, leaves, stems, and roots (FIG. 14). Based upon the foregoing discussion, the instant inventors hypothesized that NtbZIP2a and b also regulate E4/5/10, individually and/or cooperatively with NtbZIP1a and b. Thus, NtbZIP2a was tested for transactivation of the E4 promoter, individually or in combination with NtbZIP1a. More specifically, the E4 promoter was fused to the firefly luciferase reporter gene and the bZIP TFs were cloned into pBS vector under the control of the CaMV35S promoter and rbcs terminator. The results showed that, individually, both NtbZIP1a and NtbZIP2a activate the E4 promoter; however, when both NtbZIP1a and 2a were co-expressed, transactivation of the E4 promoter was significantly increased, compared to that was induced by each factor alone (FIG. 15).

Figure 16A:
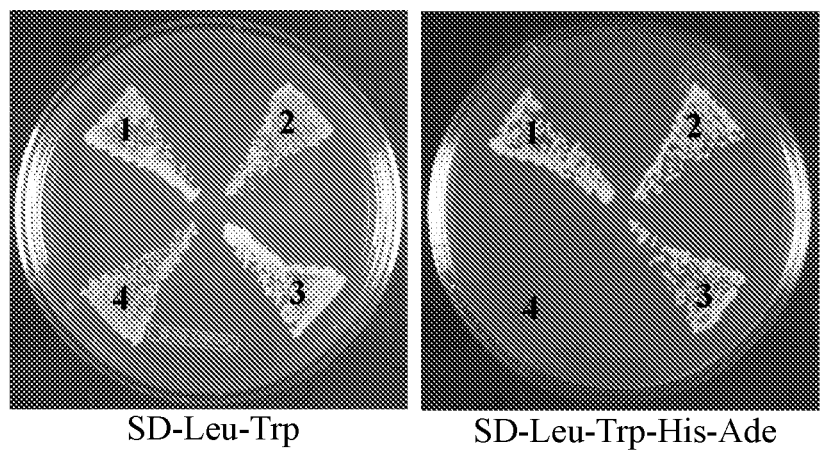
FIGS. 16A-B show images illustrating protein-protein interaction of NtbZIP1 and NtbZIP2 using yeast two hybrid assay. (A) Yeast two hybrid assay showing protein-protein interaction between NtbZIP1 and NtbZIP2. Colony growth on synthetic drop-out (SD) medium lacking leucine, tryptophan, histidine and adenine (-leu-trp-his-ade) indicates interaction between the proteins (bZIPs). (B) Schematic diagram of NtbZIP1 and NtbZIP2. The bZIP domain is indicated by "shaded" rectangle. The numbers indicate the amino acid.
Figure 16B:
Figure 16B:

Next, to determine whether NtbZIP1a/b interact with NtbZIP2a, the inventors performed yeast hybrid assay. The growth of the yeast cells on synthetic drop-out (SD) medium lacking leucine, trptophan, histidine, and adenine (SD-leu-trp-his-ade) suggests that NtbZIP1a/b interact with NtbZIP2a (FIG. 16A; 1 and 2). In addition, NtbZIP2 interacts with itself to form a homo-dimer (FIG. 16A; 3). The bZIP domains of NtbZIP1 and NtbZIP2 are illustrated in FIG. 16B.

Although the instant Example only tested NtbZIP2a activity on the E4 promoter, but not the E5 or E10 promoters, it is believed that both NtbZIP2 factors are activators of E4/5/10 genes. That is, this Example suggests that the group C NtbZIP2a and b are two previously uncharacterized regulators of E4/5/10 genes. In addition, this Example shows that NtbZIP1 and NtbZIP2 are synergistic in activation of the E4 (possibly E5 and 10) promoter. In particular, without wishing to be bound by theory, it is believed that NtbZIP2a and/or b interact with NtbZIP1a and/or b to enhance DNA binding ability and significantly increase activation of the E4/5/10 promoters, as compared to NtbZIP1 or NtbZIP2 alone.

In summary, two group S and two group C NtbZIP factors that are positive regulators of E4/5/10 genes were characterized herein. The transactivation activities of NtbZIP1a and 2a on the E4 promoter are additive. Therefore, without wishing to be bound by theory, it is believed that knockout approaches to inactivate one or all of these genes reduces E4/5/10 gene expression.

REFERENCES

[1] Gavilano, L. B., and Siminszky, B. (2007). Isolation and characterization of the cytochrome P450 gene CYP82E5v2 that mediates nicotine to nornicotine conversion in the green leaves of tobacco. Plant & cell physiology 48, 1567-1574.

[2] Higo, K., Ugawa, Y., Iwamoto, M., and Higo, H. (1998). PLACE: a database of plant cis-acting regulatory DNA elements. Nucleic acids research 26, 358-359.

[3] Leitch, I. J., Hanson, L., Lim, K. Y., Kovarik, A., Chase, M. W., Clarkson, J. J., and Leitch, A. R. (2008). The ups and downs of genome size evolution in polyploid species of Nicotiana (Solanaceae). Annals of botany 101, 805-814.

[4] Lescot, M., Dehais, P., Thijs, G., Marchal, K., Moreau, Y., Van de Peer, Y., Rouze, P., and Rombauts, S. (2002). PlantCARE, a database of plant cis-acting regulatory elements and a portal to tools for in silico analysis of promoter sequences. Nucleic acids research 30, 325-327.

[5] Lewis, R. S., Bowen, S. W., Keogh, M. R., and Dewey, R. E. (2010). Three nicotine demethylase genes mediate nornicotine biosynthesis in Nicotiana tabacum L.: functional characterization of the CYP82E10 gene. Phytochemistry 71, 1988-1998.

[6] Lim, K. Y., Matyasek, R., Kovarik, A., and Leitch, A. R. (2004). Genome evolution in allotetraploid Nicotiana. Biol J. Linn Soc 82, 599-606.

[7] Morita, M., Shitan, N., Sawada, K., Van Montagu, M. C., Inze, D., Rischer, H., Goossens, A., Oksman-Caldentey, K. M., Moriyama, Y., and Yazaki, K. (2009). Vacuolar transport of nicotine is mediated by a multidrug and toxic compound extrusion (MATE) transporter in Nicotiana tabacum. Proceedings of the National Academy of Sciences of the United States of America 106, 2447-2452.

[8] Pattanaik, S., Werkman, J. R., Kong, Q., and Yuan, L. (2010a). Site-directed mutagenesis and saturation mutagenesis for the functional study of transcription factors involved in plant secondary metabolite biosynthesis. Methods in molecular biology 643, 47-57.

[9] Pattanaik, S., Kong, Q., Zaitlin, D., Werkman, J. R., Xie, C. H., Patra, B., and Yuan, L. (2010b). Isolation and functional characterization of a floral tissue-specific R2R3 MYB regulator from tobacco. Planta 231, 1061-1076.

[10] Shoji, T., and Hashimoto, T. (2011). Tobacco MYC2 regulates jasmonate-inducible nicotine biosynthesis genes directly and by way of the NIC2-locus ERF genes. Plant & cell physiology 52, 1117-1130.

[11] Shoji, T., Kajikawa, M., and Hashimoto, T. (2010). Clustered transcription factor genes regulate nicotine biosynthesis in tobacco. The Plant cell 22, 3390-3409.

[12] Shoji, T., Inai, K., Yazaki, Y., Sato, Y., Takase, H., Shitan, N., Yazaki, K., Goto, Y., Toyooka, K., Matsuoka, K., and Hashimoto, T. (2009). Multidrug and toxic compound extrusion-type transporters implicated in vacuolar sequestration of nicotine in tobacco roots. Plant physiology 149, 708-718.

[13] Sierro, N., van Oeveren, J., van Eijk, M. J., Martin, F., Stormo, K. E., Peitsch, M. C., and Ivanov, N. V. (2013a). Whole genome profiling physical map and ancestral annotation of tobacco Hicks Broadleaf. The Plant journal: for cell and molecular biology 75, 880-889.

[14] Sierro, N., Battey, J. N., Ouadi, S., Bovet, L., Goepfert, S., Bakaher, N., Peitsch, M. C., and Ivanov, N. V. (2013b). Reference genomes and transcriptomes of Nicotiana sylvestris and Nicotiana tomentosiformis. Genome biology 14, R60.

[15] Sierro, N., Battey, J. N., Ouadi, S., Bakaher, N., Bovet, L., Willig, A., Goepfert, S., Peitsch, M. C., and Ivanov, N. V. (2014). The tobacco genome sequence and its comparison with those of tomato and potato. Nature communications 5, 3833.

[16] Siminszky, B., Gavilano, L., Bowen, S. W., and Dewey, R. E. (2005). Conversion of nicotine to nornicotine in Nicotiana tabacum is mediated by CYP82E4, a cytochrome P450 monooxygenase. Proceedings of the National Academy of Sciences of the United States of America 102, 14919-14924.

[17] Singh, S. K., Wu, Y., Ghosh, J. S., Pattanaik, S., Fisher, C., Wang, Y., Lawson, D., and Yuan, L. (2015). RNA-sequencing Reveals Global Transcriptomic Changes in Nicotiana tabacum Responding to Topping and Treatment of Axillary-shoot Control Chemicals. Scientific reports 5, 18148.

[18] Van Moerkercke, A., Steensma, P., Schweizer, F., Pollier, J., Gariboldi, I., Payne, R., Vanden Bossche, R., Miettinen, K., Espoz, J., Purnama, P. C., Kellner, F., Seppanen-Laakso, T., O'Connor, S. E., Rischer, H., Memelink, J., and Goossens, A. (2015). The bHLH transcription factor BIS1 controls the iridoid branch of the monoterpenoid indole alkaloid pathway in Catharanthus roseus. Proceedings of the National Academy of Sciences of the United States of America 112, 8130-8135.

[19] Yu, F., and De Luca, V. (2013). ATP-binding cassette transporter controls leaf surface secretion of anticancer drug components in Catharanthus roseus. Proceedings of the National Academy of Sciences of the United States of America 110, 15830-15835.

[20] Ehlert, A., et al. (2006) Two-hybrid protein-protein interaction analysis in Arabidopsis protoplasts: establishment of a heterodimerization map of group C and group S bZIP transcription factors. The Plant Journal, 46: 890-900.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

What is claimed is:

1. A method of decreasing conversion of nicotine to nornicotine in a *Nicotiana* plant, the method comprising mutating a plant genome to knockout a *Nicotiana* basic region/leucine zipper (bZIP) transcription factor comprising an amino acid sequence selected from the group consisting of SEQ ID NO: 2, 4, 5, and 6; and measuring expression of genes encoding nicotine demethylases, measuring nicotine levels, measuring nornicotine levels, and/or measuring N-nitrosonornicotine levels in the *Nicotiana* plant.

2. The method of claim 1, wherein the *Nicotiana* bZIP transcription factor is a group C bZIP transcription factor.

3. The method of claim 1, wherein the *Nicotiana* bZIP transcription factor is NtbZIP1a (SEQ ID NO: 2).

4. The method of claim 1, comprising mutating the plant genome to knockout at least two of the *Nicotiana* bZIP transcription.

5. The method of claim 1, wherein the *Nicotiana* bZIP transcription factor is a group S bZIP transcription factor.

6. The method of claim 1, wherein the *Nicotiana* bZIP transcription factor is NtbZIP1b (SEQ ID NO: 4).

7. The method of claim 1, wherein the *Nicotiana* bZIP transcription factor is NtbZIP2a (SEQ ID NO: 5).

8. The method of claim 1, wherein the *Nicotiana* bZIP transcription factor is NtbZIP2b (SEQ ID NO: 6).

* * * * *